US008612257B2

(12) United States Patent
Zaitsu et al.

(10) Patent No.: US 8,612,257 B2
(45) Date of Patent: Dec. 17, 2013

(54) MEDICAL PUMP MONITORING SYSTEM

(75) Inventors: Akinori Zaitsu, Kasuga (JP); Kou Ishikawa, Ashigarakami-gun (JP); Kenji Nakahara, Shibuya-ku (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 2780 days.

(21) Appl. No.: 10/820,840

(22) Filed: Apr. 9, 2004

(65) Prior Publication Data

US 2004/0193328 A1    Sep. 30, 2004

Related U.S. Application Data

(62) Division of application No. 09/864,394, filed on May 25, 2001, now abandoned.

(30) Foreign Application Priority Data

May 26, 2000 (JP) ................................. 2000-161155
Nov. 15, 2000 (JP) ................................. 2000-352537

(51) Int. Cl.
*G06Q 50/00* (2012.01)

(52) U.S. Cl.
USPC .......................................................... 705/3

(58) Field of Classification Search
USPC ......... 604/65–67, 891.1, 892.1; 700/2; 705/2, 705/3
See application file for complete search history.

(56) References Cited

U.S. PATENT DOCUMENTS

| | | |
|---|---|---|
| 4,291,692 A | 9/1981 | Bowman et al. |
| 4,756,706 A | 7/1988 | Kerns et al. |

(Continued)

FOREIGN PATENT DOCUMENTS

| | | | |
|---|---|---|---|
| AU | 199929073 | * | 12/1999 |
| AU | 199929073 A1 | | 12/1999 |

(Continued)

OTHER PUBLICATIONS

Akinori Zaitsu et al., "An Infusion Robot (Prototype II)", Anesthesia—Intensive Care and Their Technology, 1993, Kokuseido Publication Co., Ltd., Tokyo, Japan, Jul. 1, 1993, pp. 146-152.

*Primary Examiner* — Matthew F Desanto
(74) *Attorney, Agent, or Firm* — Buchanan Ingersoll & Rooney PC

(57) ABSTRACT

A medical pump monitor system in which an infusion circuitry creation unit setting/changing the connection conditions of infusion lines from a plurality of medical pumps, and administration passes and/or administration positions for a patient is provided, and it is made possible to display infusion circuitry data created in the infusion circuitry creation unit on a monitor screen by operations by an operator of the medical pump monitor system. And, a real-time monitoring system performing real time communication with external apparatuses including one or more medical apparatuses, and controlling the external apparatuses and/or displaying the conditions of the external apparatuses, including a communication unit communicating with external apparatuses, a display unit displaying the conditions of the external apparatuses, storing unit storing one or more past communication data obtained by the communication unit, a comparison unit comparing currently communicated data with past data, and a control unit controlling contents to be displayed on the display unit based on signals from the comparison unit, in which the comparison unit reduces the amount of the data for the amount of signals to be sent to the control unit, in the case where the past data and the current data are identical to each other in comparison with the case where the past data and the current data are different from each other.

11 Claims, 25 Drawing Sheets

(56) References Cited

U.S. PATENT DOCUMENTS

| | | |
|---|---|---|
| 5,338,157 A | 8/1994 | Blomquist |
| 5,507,412 A | 4/1996 | Ebert et al. |
| 5,544,661 A | 8/1996 | Davis et al. |
| 5,651,775 A | 7/1997 | Walker et al. |
| 5,713,856 A | 2/1998 | Eggers et al. |
| 5,782,805 A * | 7/1998 | Meinzer et al. ............... 604/131 |
| 5,935,078 A | 8/1999 | Feierbach |
| 6,146,523 A | 11/2000 | Kenley et al. |
| 6,151,581 A | 11/2000 | Kraftson et al. |
| 6,413,233 B1 | 7/2002 | Sites et al. |
| 6,671,563 B1 * | 12/2003 | Engelson et al. ................. 700/2 |
| 7,109,878 B2 * | 9/2006 | Mann et al. .................... 604/131 |
| 2001/0049608 A1 | 12/2001 | Hochman |
| 2003/0046285 A1 | 3/2003 | Gruenwald |

FOREIGN PATENT DOCUMENTS

| | | |
|---|---|---|
| EP | 0960627 A2 | 12/1999 |
| JP | 5-7623 A | 1/1993 |
| JP | 11-502132 A | 2/1999 |
| JP | 11-347118 | 12/1999 |
| WO | WO 96/28209 A1 | 9/1996 |

* cited by examiner

F I G. 4A
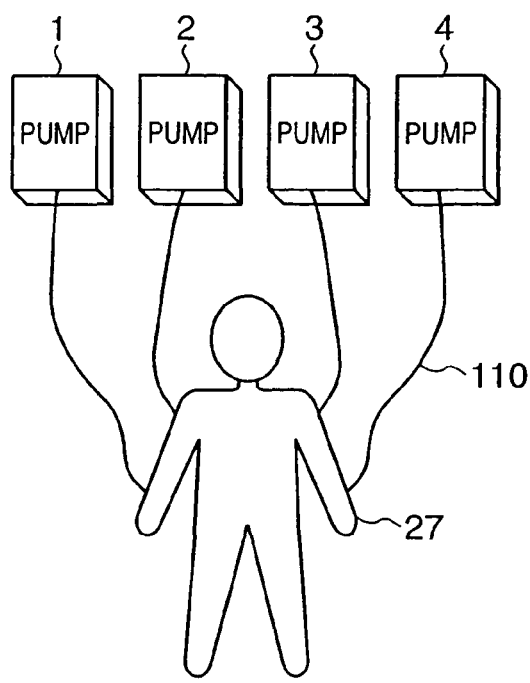
F I G. 4B
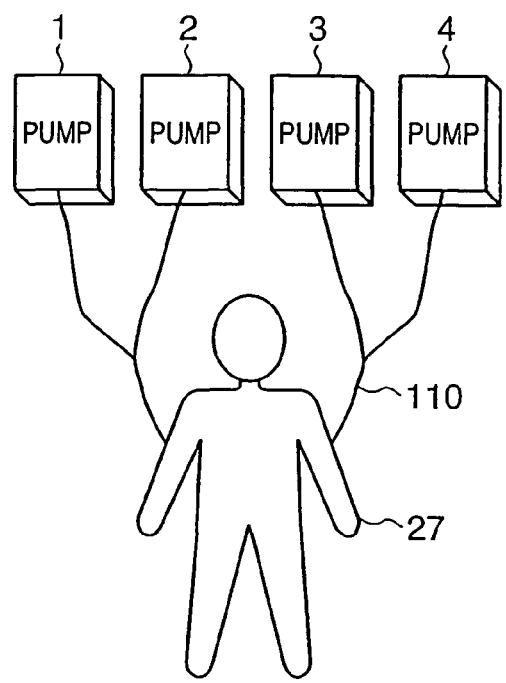
F I G. 4C
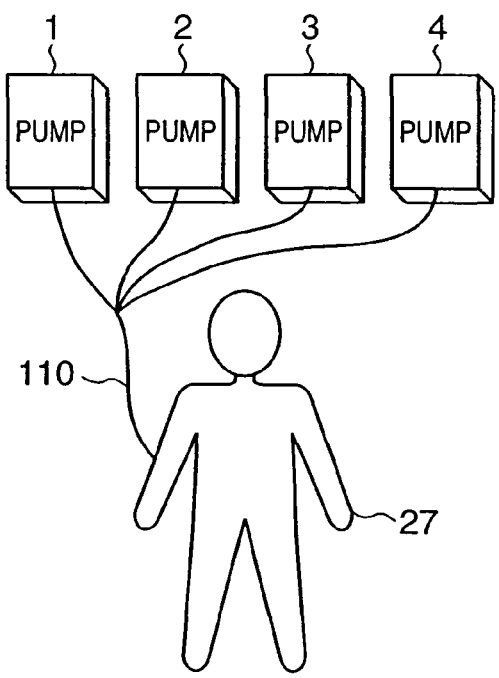

FIG. 5
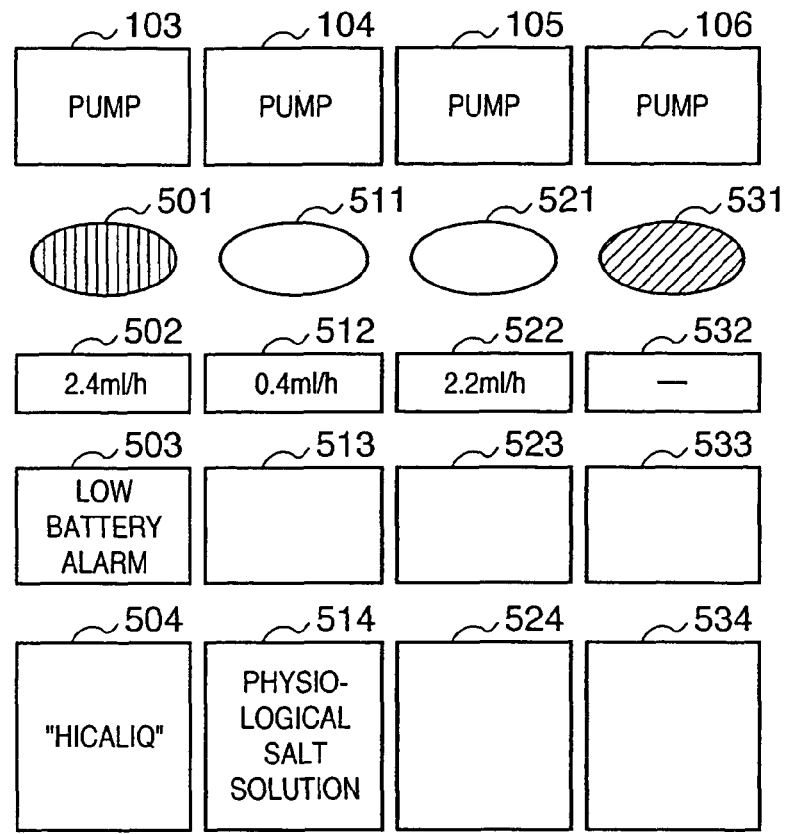
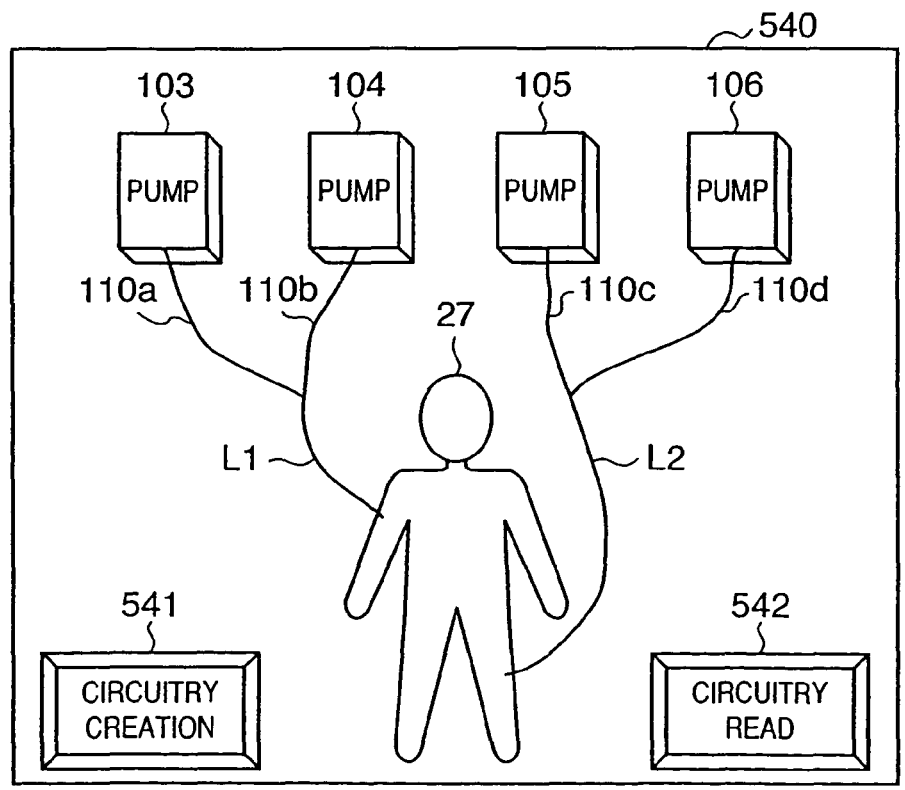

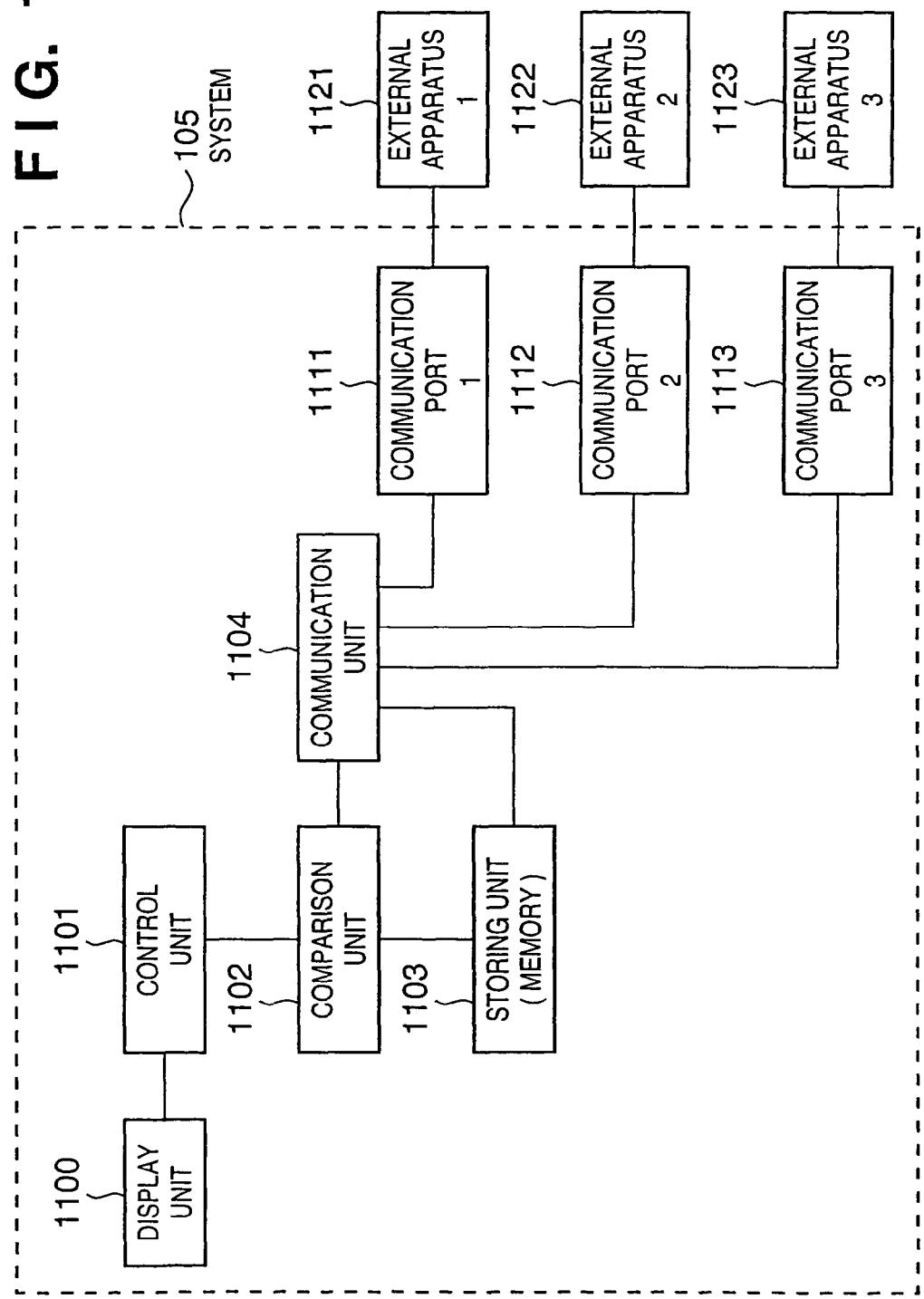

CALCULATION OF INVERSE BCC $BCC1 = 1 ⊻ 2 ⊻ 3 ⊻ 4 \cdots ⊻ n$ $BCC2 = \overline{1} + \overline{2} + \overline{3} + \overline{4} \cdots + \overline{n}$

LOWER TWO BYTES ARE USED

MEMORY MAP

MECHANISM OF HIGH SPEED

· INVERSE BCC CHECK MODE

MEDICAL PUMP MONITORING SYSTEM

FIELD OF THE INVENTION

The present invention relates to a medical pump monitor system administering medical fluids using a plurality of medical pumps for one patient, and managing information of these medical pumps collectively, a controlling method therefore, and a computer-readable memory associated with control thereof. The present invention also relates to a real-time monitoring system performing real-time communication with external apparatuses including one or more medical apparatuses to control such external apparatuses and/or display the conditions thereof, a controlling method therefore, and a computer-readable memory (storage medium) storing therein a control program thereof.

BACKGROUND OF THE INVENTION

Varieties of therapies and drugs for use in those therapies have emerged and administration methods have become complicated due to recent advancement of medical treatments. Accordingly, therapies in which a plurality of medical pumps (syringe pump and infusion pump) is used at a time for one patient are on the increase. Also, systems managing the flows of administered medical fluids from plurality of such medical pumps and alarm information such as a drop in residual low battery/occlusion of an infusion line have been proposed.

A system in which visual contact is made with the displayed states of alarms in such a medical pump system is disclosed in Japanese Patent Laid-open No. 5-7623 specification.

A schematic diagram of a system in which medical pumps independent of one another are connected to a personal computer via communication cables, and flow volumes and alarm information of the medical pumps are collected and displayed as application software of the personal computer is shown in FIG. 2.

Also, a schematic diagram of a type of a pump monitor system in which pumps share a power supply line and a data communication line with one another through a power connector 53 and a communication connector 54, and medical pumps 51 and 52 are connected in such a manner that they are stacked one after another on a base unit 55 comprising a display unit 101 on which the flow and alarm information for each pump is shown in FIG. 3.

Furthermore, in the case of such a system, in addition to collection of pump information, control such as stop/start of infusion by pumps and change of flows can also be performed from the personal computer and the base unit.

FIG. 2 shows a conventional medical pump system, wherein reference numeral 20 denotes a personal computer with system application software installed therein, reference numeral 21 denotes a display device (display unit) such as a CRT and a liquid crystal monitor connected to the personal computer, reference numeral 22 denotes communication port expanding means such as a multiplexer for expanding communication ports of RS 232C that are typically provided with only one or two channels to 4 channels, 8 channels or the like, and reference numerals 23, 24, 25 and 26 denote medical pumps. Also, reference numeral 27 denotes a patient, and medical pumps of 23 to 26 deliver individual set liquid medicines into the patient.

FIGS. 4A to 4C show cases where the same number of medical pumps as in FIG. 2 are used to perform administration for one patient, wherein their administration passes are different from one another due to the condition of the patient, administrated drugs and the like. For example, FIG. 4A shows a case where four pumps each have individual infusion lines and drugs are injected into different points of the patient, and FIG. 4B shows a case where two infusion lines of four medical pumps are connected with each other and the other two infusion lines are also connected with each other. Also, FIG. 4C shows a case where four medical pumps are all integrated into one line to carry out administration for the patient.

It is important in safe administration that the state of the infusion line is ascertained correctly, and there are various patterns as to states of infusion lines as administration passes to the patient in this way, but in fact, it becomes very difficult to identify the points of the patient into which the medical fluid is injected if infusion lines running from a plurality of pumps are connected with one another and cross one another.

However, conventional pump monitor systems have no functions to display infusion lines on the system, thus making it difficult to ascertain the state of infusion lines correctly.

Also, on the other hand, when a system in which one or more external apparatuses (hereinafter also referred to as "slaves") such as infusion pumps, syringe pumps, blood-pressure monitors and urinary volume monitors are connected to a host machine to manage and display the operation conditions of the apparatuses is built, works of:
(1) setting a communication protocol of nodes
(2) sending a request command
(3) receiving data and confirming the reception
(4) carrying out control in accordance with data are performed at the host machine side.

As a matter of course, the loads on the CPU of the host machine are increased if these processing are performed at high speed, and real time quality is compromised if a large number slaves are connected. Also, even if a system is made such that processing is distributed over a plurality of CPUs like a CPU (main CPU) engaged in processing of controlling and displaying slave conditions in the host machine and CPUs (sub CPUs) engaged in communication with each slave, enormous development costs are required for both main and sub CPUs due to addition of slaves and change of specifications, although processing at the main CPU is slightly curtailed.

SUMMARY OF THE INVENTION

The present invention has been made in the light of problems as described above, and its object is to provide a system in which the operation conditions of a plurality of medical pumps are monitored for one patient with a function of creating and editing an infusion line from the pump to the patient on each-by-each basis, and display information created and edited by means of this function on the system, thereby making it more easy to confirm the current states of infusion lines.

Another object of the present invention is to provide a function of capturing hand written diagrams and so on together with the function of creating and editing the infusion line, and an operator is allowed to make a choice on whether the function of creating and editing the infusion line is used to create the infusion line, or handwritten diagrams and so on are captured in the system to display the same, thus making it possible display various cases of the infusion line on the medical pump monitor system.

Still another object of the present invention is to provide a real-time monitoring system, a controlling method therefore and a program storage medium, which enable real-time monitoring of the operation states, arrangement/connection states, alarm information of a plurality of medical apparatuses such as infusion pumps, syringe pumps, blood monitors, urinary volume monitors, water contents of medical fluids, states of intake and output of electrolytes and so on.

Other features and advantages of the present invention will be apparent from the following descriptions taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the descriptions, serve to explain the principle of the invention.

FIG. 4A shows one of block diagrams of infusion circuitry patterns in the first embodiment of the present invention;

FIG. 4B shows one of block diagrams of infusion circuitry patterns in the first embodiment of the present invention;

FIG. 4C shows one of block diagrams of infusion circuitry patterns in the first embodiment of the present invention;

FIG. 5 shows a medical pump monitor screen in the first embodiment of the present invention;

FIG. 11 is a block diagram in the second embodiment of the present invention;

DETAILED DESCRIPTION OF THE PREFERRED EMBODIMENTS

First Embodiment

Figure 1:
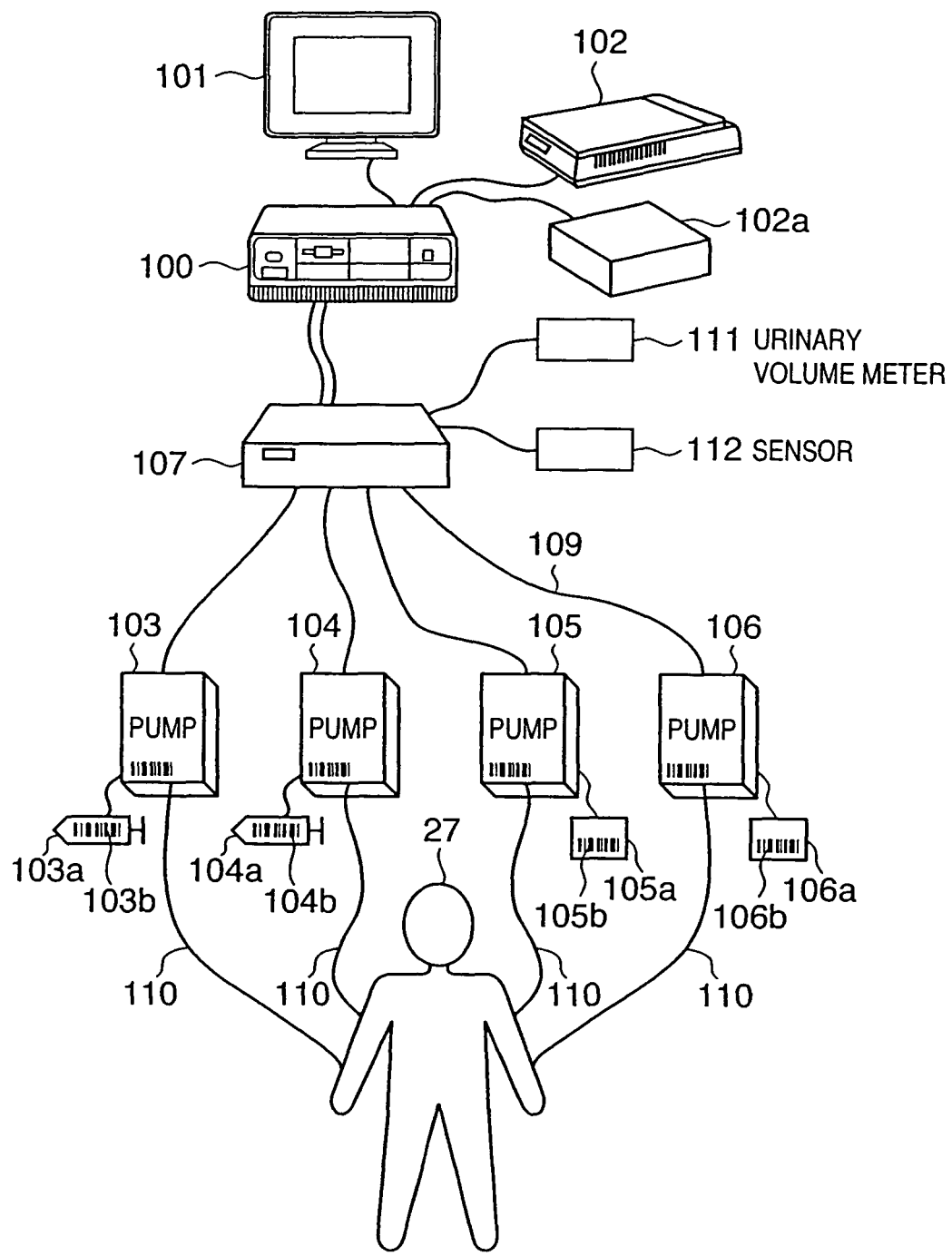
FIG. 1 shows a block diagram of a medical pump system in the first embodiment of the present invention.
Figure 2:
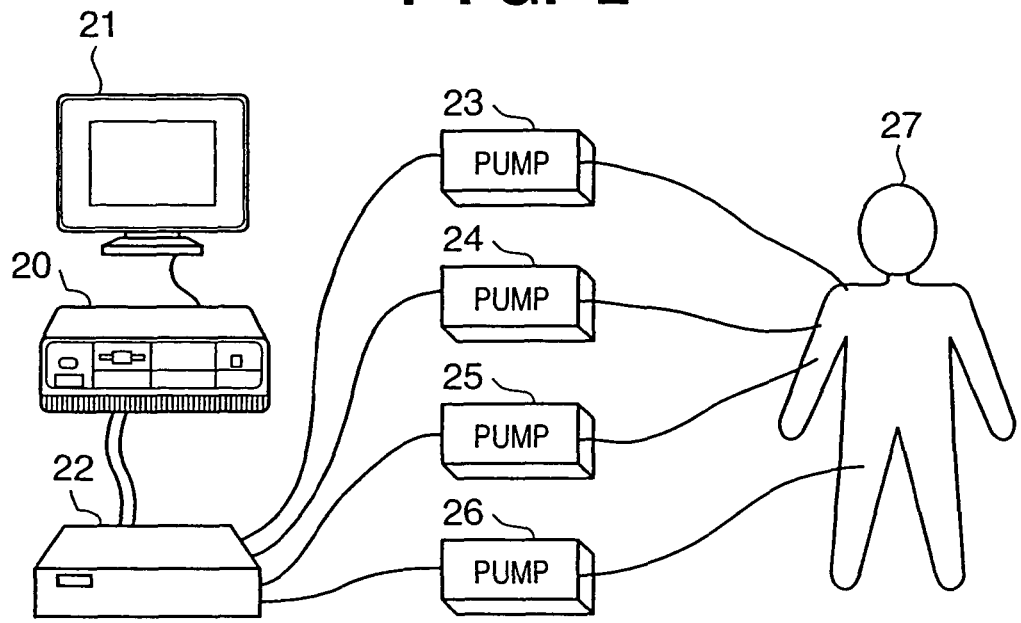
FIG. 2 shows a block diagram of the medical pump system in prior arts.
Figure 3:
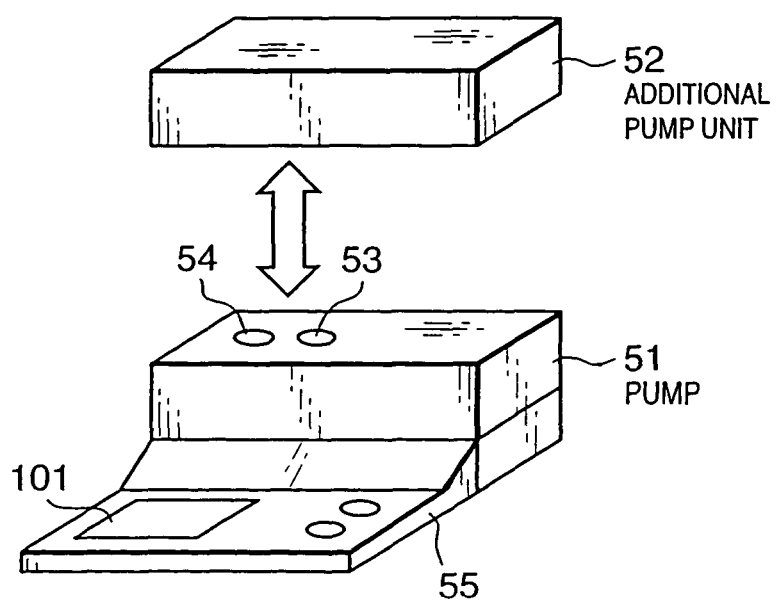
FIG. 3 shows a block diagram of a medical pump system of another embodiment in prior arts.

Examples of specific embodiments of the present invention will be described below. A block diagram of a medical pump system of the present invention is shown in FIG. 1. In this embodiment, an example of collecting and managing information of four medical pumps is described.

Reference numeral 100 denotes a controller (control unit), which makes up a central portion of this medical pump monitor system, and for the controller, a personal computer having an inputting device such as a keyboard and a pointing device such as a mouse is usually used. Reference numeral 101 denotes a display (display unit), which displays flow values and alarm information for a plurality of medical pumps of 103, 104, 105 and 106, collected by the controller 100, and the urinary volume from urinary volume meters 111 and the amount of electrolytes ($Na^+$, $Ca^{2+}$, $K^+$, $Cl^-$) from catheter type censor 112, and displays infusion lines.

Figure 9:
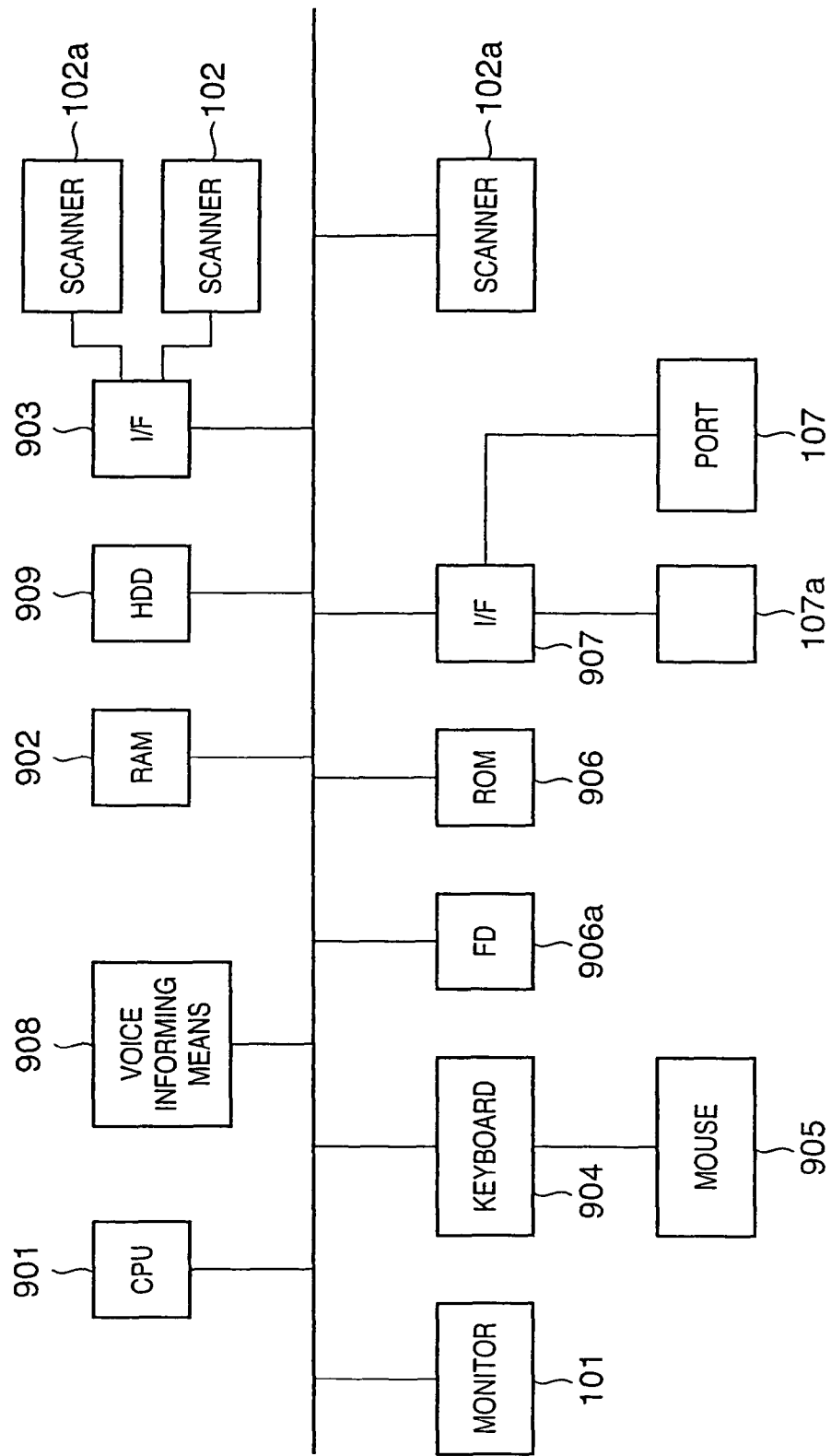
FIG. 9 shows an example of a configuration of a control unit 100 in FIG. 1.

In the case where the personal computer is used as the controller 100, a CRT or a liquid crystal monitor is used for the display (display unit) 101. Reference numeral 102 denotes a scanner (reading means) for capturing handwritten information of infusion lines, and reference numeral 102a denotes a scanner for reading product identification information (such as bar codes), and they are connected to the controller 100. Reference numeral 107 denotes communication port expansion device (communication port expanding means) such as a multiplexer for multiplying communication ports when the controller 100 is poorly equipped with ports for communicating with pumps that collect data. The controller 100 is connected to medical pumps 103, 104, 105 and 106 via this communication port expansion device 107 using a communication cable (wired) 109 or is connected therewith wirelessly. The configuration of the controller 100 is, for example a configuration as shown in FIG. 9, which comprises a CPU 901, a RAM 902, a ROM 906, a HDD 909, a floppy disk (FD) 906a, a keyboard 904 and a mouse 905, and is connected to a display 101 and is connected via an I/F 903 to the scanner 102. It is further connected via an I/F 907 to the communication port expansion device 107. Also, it is connected to the host computer of a nurse station or the like through an external communication port 107*a*.

When the medical pump monitor system is started normally, the controller 100 urges an operator to select information of drugs to be administered by respective pumps from a drug database (drug library) file stored in the memory means in the controller 100. The operator (medical staff such as a doctor and nurse) selects drugs to be administered such as a vitamin solution for the pump 103, a physiological salt solution for the pump 104 and high calorie medical fluids containing electrolytes such as $Na^+$, $Ca^{2+}$, $K^+$, $Cl^-$ for the pump 105. Alternatively, the operator inputs product identification information to the system as medical apparatus identification information (such as bar codes) stuck on respective medical pumps using the scanner 102*a* for respective medical pumps 103 to 106, and reads product identification information to the system as drug identification information (such as bar codes) 103*b*, 104*b*, 105*b* and 106*b* syringes 103*a* and 103*b* in which drugs are taken in predetermined minutes and which are connected to the pumps or fluid containers 105*a* and 106*a* connected to the pumps to make a check on whether or not the drug is one included in the drug database file of the controller 100. When the medical pump is not connected, voice information is given by voice informing means 908 for calling attention if it is a drug not included in the database file. The identification information of this pump and the drug identification information are stored in the RAM 902 as a pair, and are displayed together on the display unit 101 as shown in FIG. 5. When selection of drugs is completed, the controller 100 communicates with four pumps connected as medical pumps 103, 104, 105 and 106 in succession at a fixed time interval (for example one minute interval), wirelessly and/or with cables.

The communication is data for requesting information of current flows of administered fluids from respective medical pumps 103, 104, 105 and 106, and when the request data are received by the pumps, the pumps send back the flow information to the controller 100 in predetermined format. The controller 100 subsequently sends signals requesting alarm information to the connected medical pumps 103, 104, 105 and 106, and when they are received by the pumps, the pumps also send back the alarm information to the controller 100 based on a predetermined format. Furthermore, if there exists no alarm information, then a signal indicating no alarm information is sent back to the controller 100.

The controller 100 displays information from connected medical pumps 103 to 106 on the display (display unit) in such a manner that it is displayed along a pump information display area shown in FIG. 5. In FIG. 5, a region denoted by reference numeral 501 is a region in which operation states of medical pumps 103 to 106 are indicated by color, for example by green during normal operations (described with blank in this figure), by red when an alarm is given (described with vertical lines in this figure), by yellow in the case when administration operations are interrupted (described with slashes in this figure) and by gray when the pump itself is not connected. Also, its contents (occlusion, abnormal flows, etc.) are displayed at the same time. A region denoted by reference numeral 502 is a region in which the flow value of the pump 103 is indicated. Reference numeral 503 denotes a region in which alarm information currently occurring in the medical pump 103 is indicated, and the region is blanked when no alarm is given. Reference numeral 504 denotes a region in which drugs that are administered are displayed. The system can be operated even if drugs to be administered are not defined, but in this case, the region is blanked.

In a similar way, reference numerals 511 to 514 denote regions in which information about the medical pump 104 is displayed, reference numerals 521 to 524 denote regions in which information about the medical pump 105 is displayed, and reference numerals 531 to 534 denote regions in which information about the medical pump 106 is displayed.

Reference numeral 540 denotes an infusion circuitry display region (infusion circuitry display unit), a region in which a graphic file stored in the controller 100 in predetermined format and file name is displayed. The graphic file may be a general graphic file such as a bit map file and a JPG file in the case where the controller 100 is a personal computer or the like. In this embodiment, a bit map file of 24 bits color with 640 dots (lateral direction)×480 dots (vertical direction) is stored in file name of "C:¥Yuekic.bmp".

In the case where any file to be displayed in the infusion circuitry display region 540 does not exist in the controller 100, nothing is displayed, or "No infusion circuitry file" is displayed at the center of the region.

Reference numeral 541 denotes a circuitry creation function calling button (circuitry creation function calling means), and by clicking (pressing) the button, an application for creating and modifying infusion circuitry and storing the same as graphic file data, as described later, is started. Reference numeral 542 denotes a circuitry read function calling button (circuitry read function means), and by clicking (pressing) the button, an application for reading a diagram of infusion circuitry and storing the same as graphic file data, as described later, is started. Furthermore, since both buttons 541 and 542 are expedient buttons displayed on the screen, the click (press) operations are operations of moving a pointer of a pointing device such as a mouse onto the button displayed on the screen and clicking the same.

A condition displayed in FIG. 5 is based on the assumption that a bit map file for displaying infusion circuitry is stored in advance, and information of the medical pump 103 is displayed in the regions 501 to 504. In a similar way, a square denoted by numeral 104 corresponds to the medical pump 104 of which information is displayed in the regions 511 to 514, a square denoted by numeral 105 corresponds to the medical pump 105 of which information is displayed in the regions 521 to 524, and a square denoted by numeral 106 corresponds to the medical pump 106 of which information is displayed in the regions 531 to 534.

By watching the diagram of infusion circuitry in the infusion circuitry display region 540, it can be understood that infusion lines 110 running from the medical pump 103 and the medical pump 104 are integrated into one line to form a first infusion line L1 to be fixed in administration position near the right brachium part of the patient 27, and infusion lines 110 running from the medical pump 105 and the medical pump 106 are integrated into one line to form a second infusion line L2 to be fixed in administration position near the left thigh part of the patient 27.

A diagram of infusion circuitry should be reregistered not only in cases where administration is started for a new patient, but also in cases where administration passes are changed due to change of drugs to be administered for long-term administration.

For registration of the diagram of infusion circuitry, a "C:¥Yuekic.bmp" file may be created anew. In this embodiment, the "C:¥Yuekic.bmp" file can be created either by clicking the circuitry creation function calling button 541 or by clicking the circuitry read function calling button 542.

Figure 6:
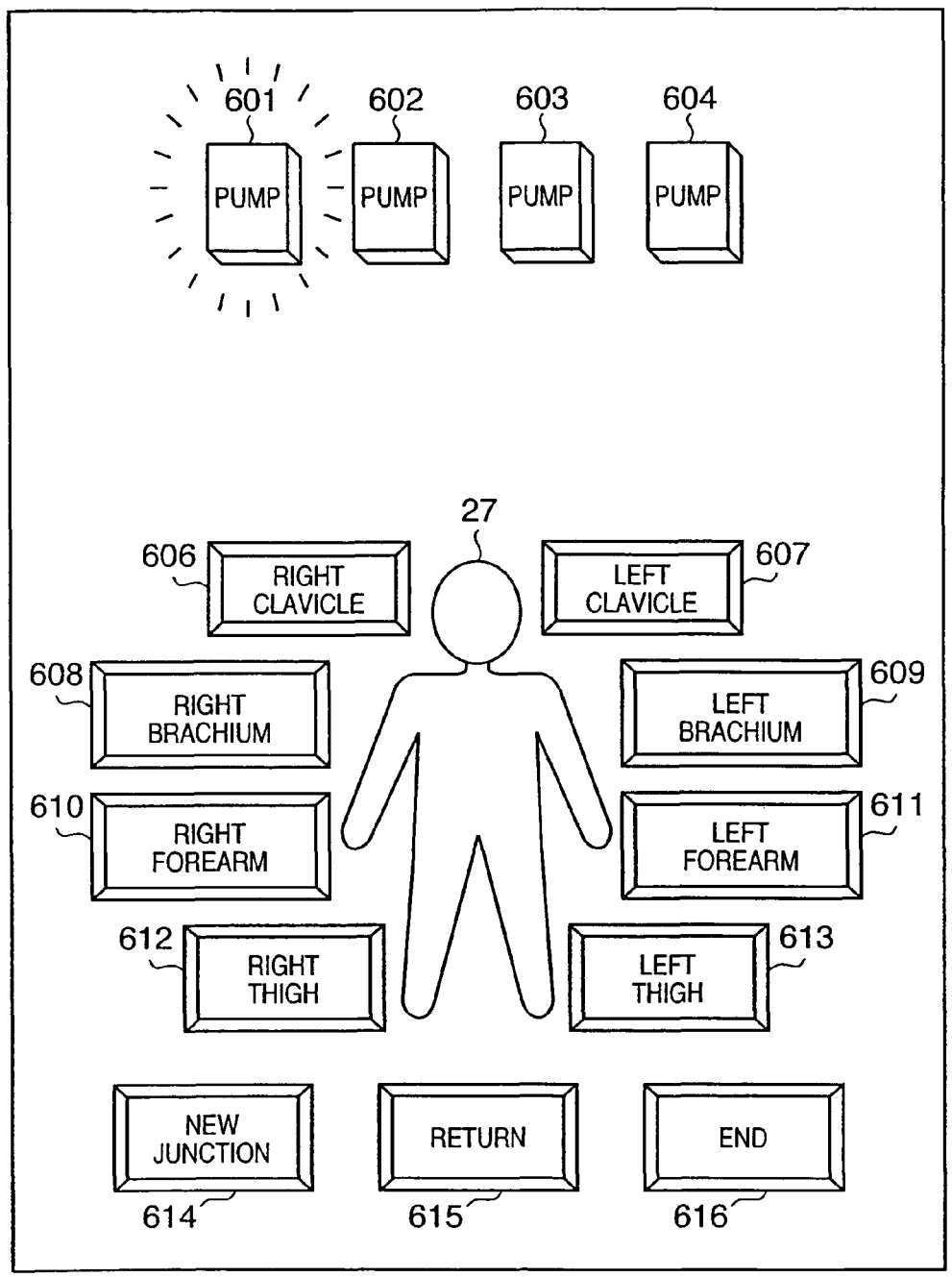
FIG. 6 shows a screen for creating infusion circuitry in a medical pump monitor system in the first embodiment of the present invention.

When the circuitry creation function calling button 541 is clicked, a window is displayed on the display unit as shown in FIG. 6. The arrangement of the pumps 103 to 106 is displayed by selecting from a plurality of arrangement patterns stored in memory means that is the most suitable for the therapy for the patient. In FIG. 6, reference numerals 601 to 604 denote medical pumps as shown in the region 540 in FIG. 5. Reference numeral 27 denotes a model showing the body of the patient, reference numerals 606 to 613 around the patient 27 denote buttons (selecting means) for selecting the portion of the patient 27 into which injection is made by the infusion line, and reference numerals 606, 607, 608, 609, 610, 611, 612 and 613 correspond to a right clavicle, left clavicle, right brachium part, left brachium part, right forearm part, left forearm part, right thigh part and left thigh part, respectively.

Reference numeral 614 denotes a junction production button (junction producing means), reference numeral 615 denotes a button for making a return by one action in case of erroneous operations, and reference numeral 616 denotes an end button (end inputting means) for overwriting the infusion circuitry diagram graphic file "C:¥Yuekic.bmp".

Figure 10B:
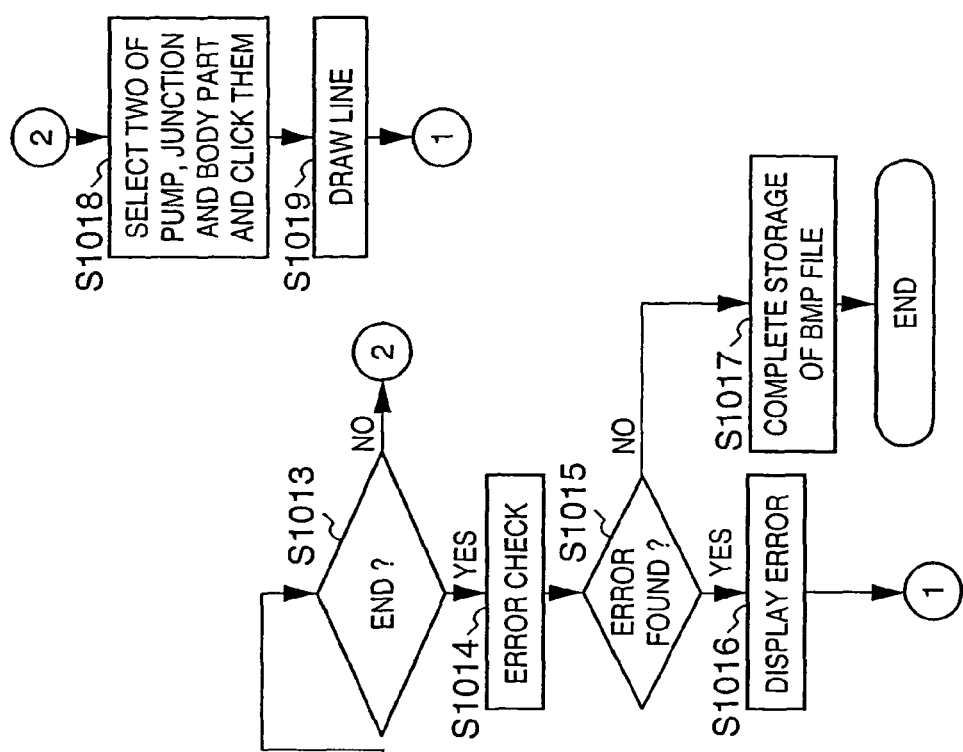
FIG. 10B is a flowchart showing the flow of infusion circuitry creation processing in the first embodiment of the present invention.
Figure 10A:
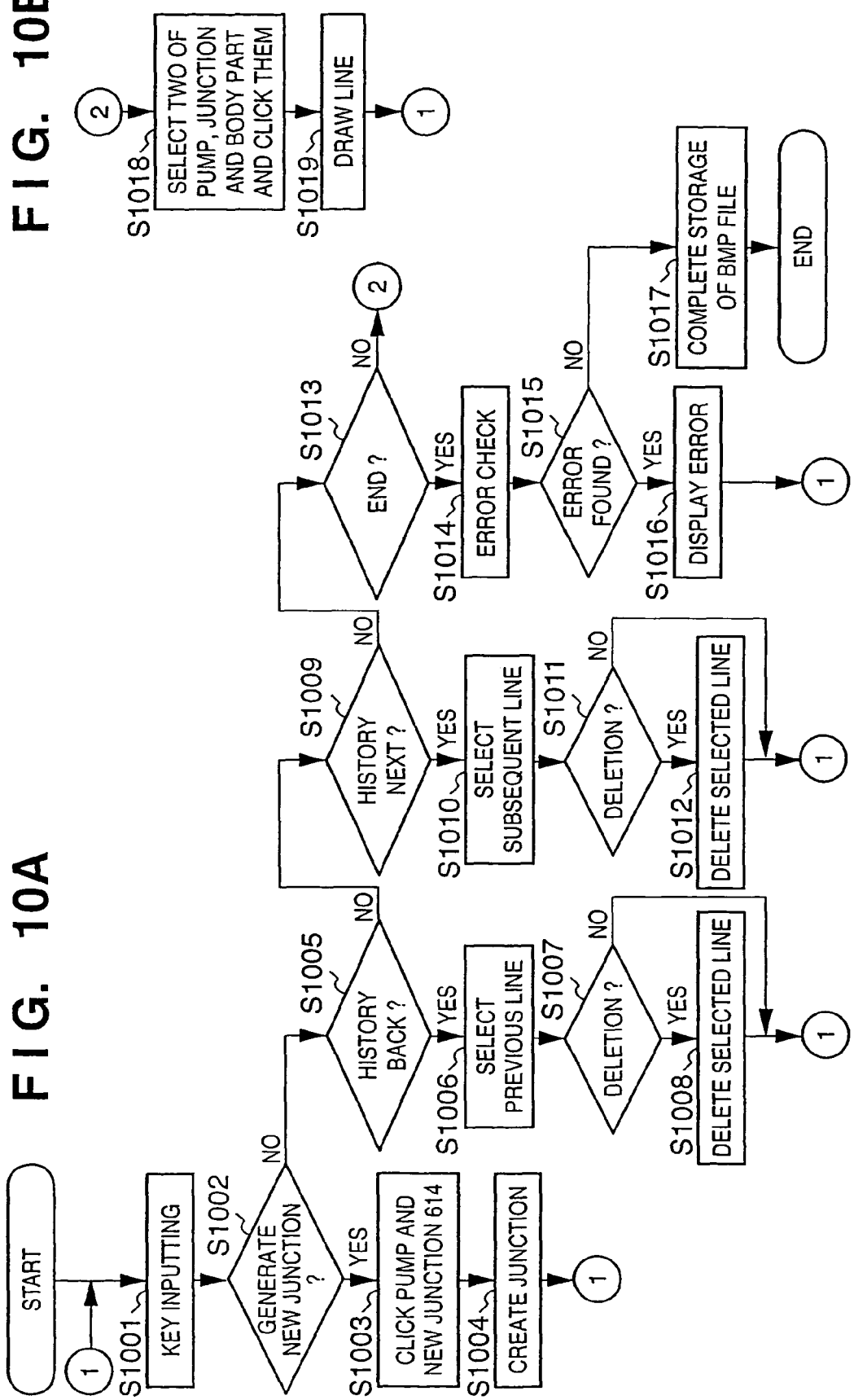
FIG. 10A is a flowchart showing a flow of infusion circuitry creation processing in the first embodiment of the present invention.

From this screen, a procedure of creating an infusion circuitry diagram as shown in the region 540 in FIG. 5 will be described based on FIG. 6 and FIGS. 7A to 7G, in correspondence with a flow of processing shown in FIGS. 10A and 10B. For creating the infusion line, the start and end points of the line may be defined one after another. Furthermore, flowcharts shown in FIGS. 10A and 10B may be stored in a ROM 906 or a HDD 909 as a program, or may be stored in a CD-ROM, a DVD-ROM, a floppy disk or the like.

Figure 7A:
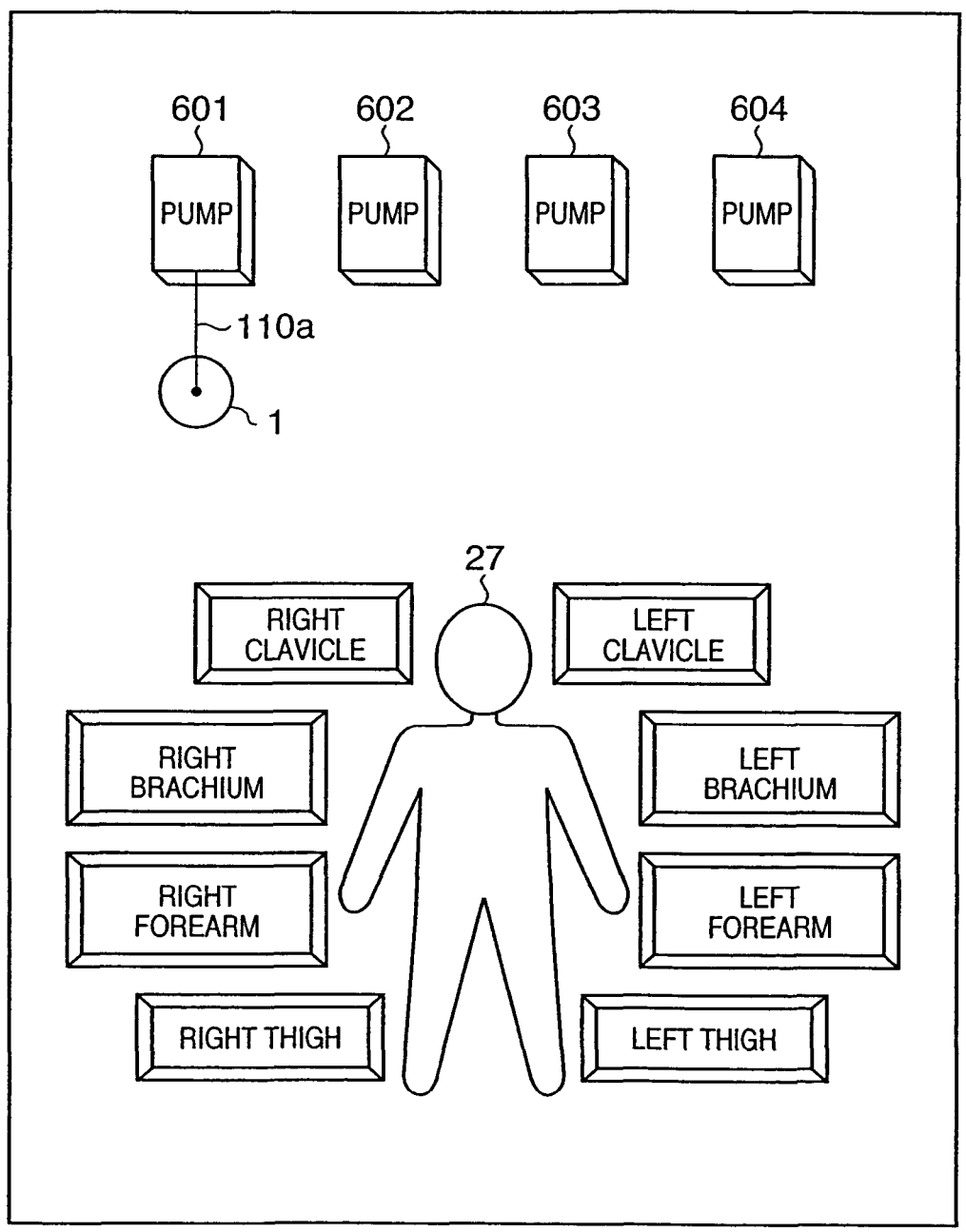
FIG. 7A shows the screen for creating infusion circuitry in the medical pump monitor system in the first embodiment of the present invention.
Figure 7B:
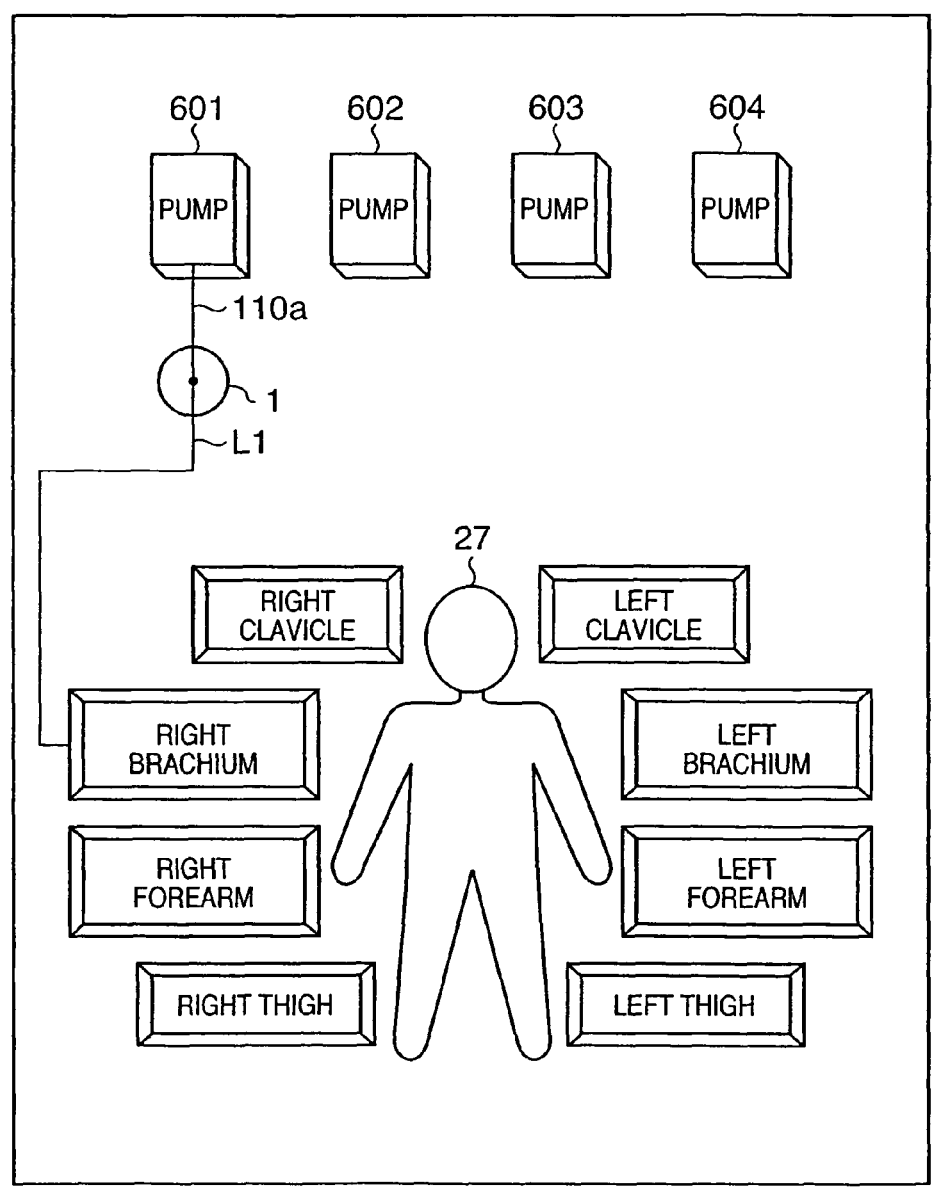
FIG. 7B shows the screen for creating infusion circuitry in the medical pump monitor system in the first embodiment of the present invention.

First, the medical pump 601 is clicked. When it is clicked, the medical pump goes into a selection state in which its displayed color is changed or it blinks (FIG. 6, S1003). Since the medical pump 601 is connected to the medical pump 602, the infusion line is created up to the junction 1 with the medical pump 602. For this purpose, the operator subsequently clicks the junction production button (junction producing means) 614 (S1003). Then, the junction is displayed just below the medical pump 601 with the junction being surrounded by a circle, and an infusion line 110a is formed in the middle between the medical pump 601 and the junction 1 (FIG. 7A, S1004).

Figure 7C:
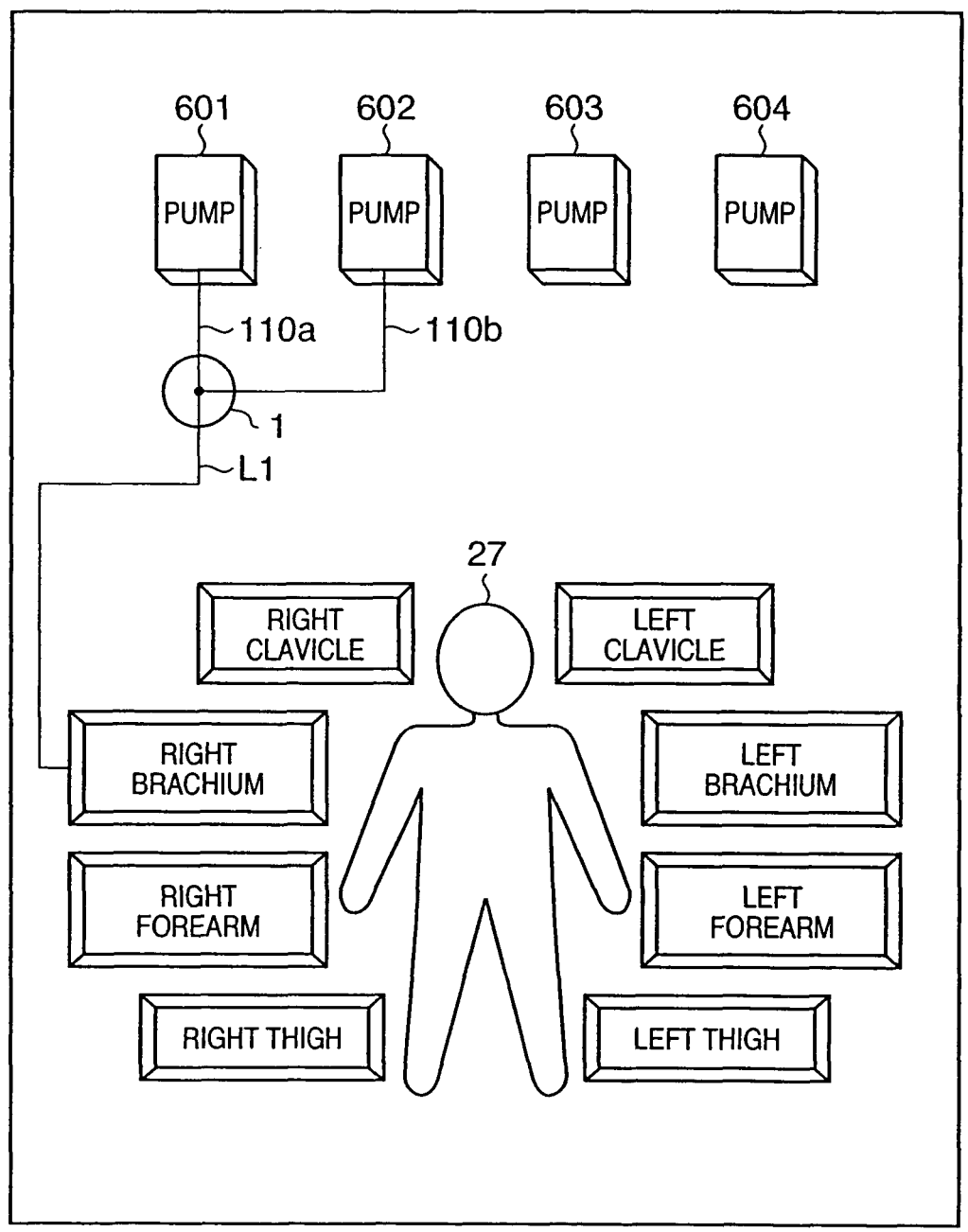
FIG. 7C shows the screen for creating infusion circuitry in the medical pump monitor system in the first embodiment of the present invention.

Since the medical pump 602 and the right brachium part of the patient 27 are connected to the junction produced at this time, then two lines may be drawn from this junction 1. For this purpose, the junction 1 surrounded by the circle is first clicked. In this condition, the junction 1 goes into the selection state (the color inside the circle highlighted, and so on), and subsequently a right brachium part selection button 608 is clicked (S1018). Furthermore, the order of clicking the junction and the right brachium part selection button in this case may be reversed. In this way, the first infusion line L1 is formed from the junction 1 to the right brachium part of the patient (state shown in FIG. 7B, S1019). Subsequently, the junction 1 and the medical pump 602 are clicked one after another, whereby an infusion line 10b is formed from the junction 1 to the medical pump 602 (FIG. 7C, S1018, S1019). In this case, the order of clicking may be reversed as well.

Figure 7D:
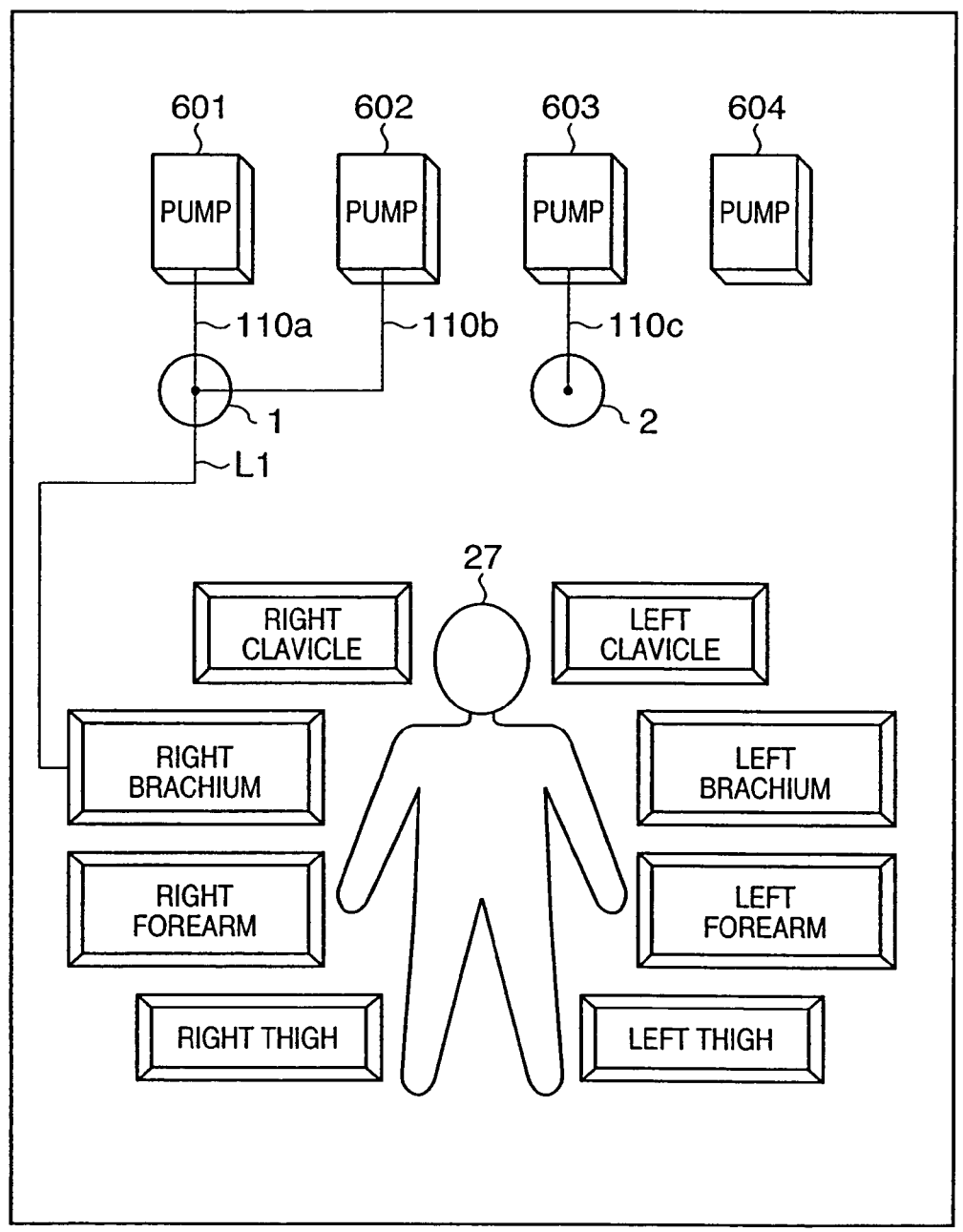
FIG. 7D shows the screen for creating infusion circuitry in the medical pump monitor system in the first embodiment of the present invention.
Figure 7E:
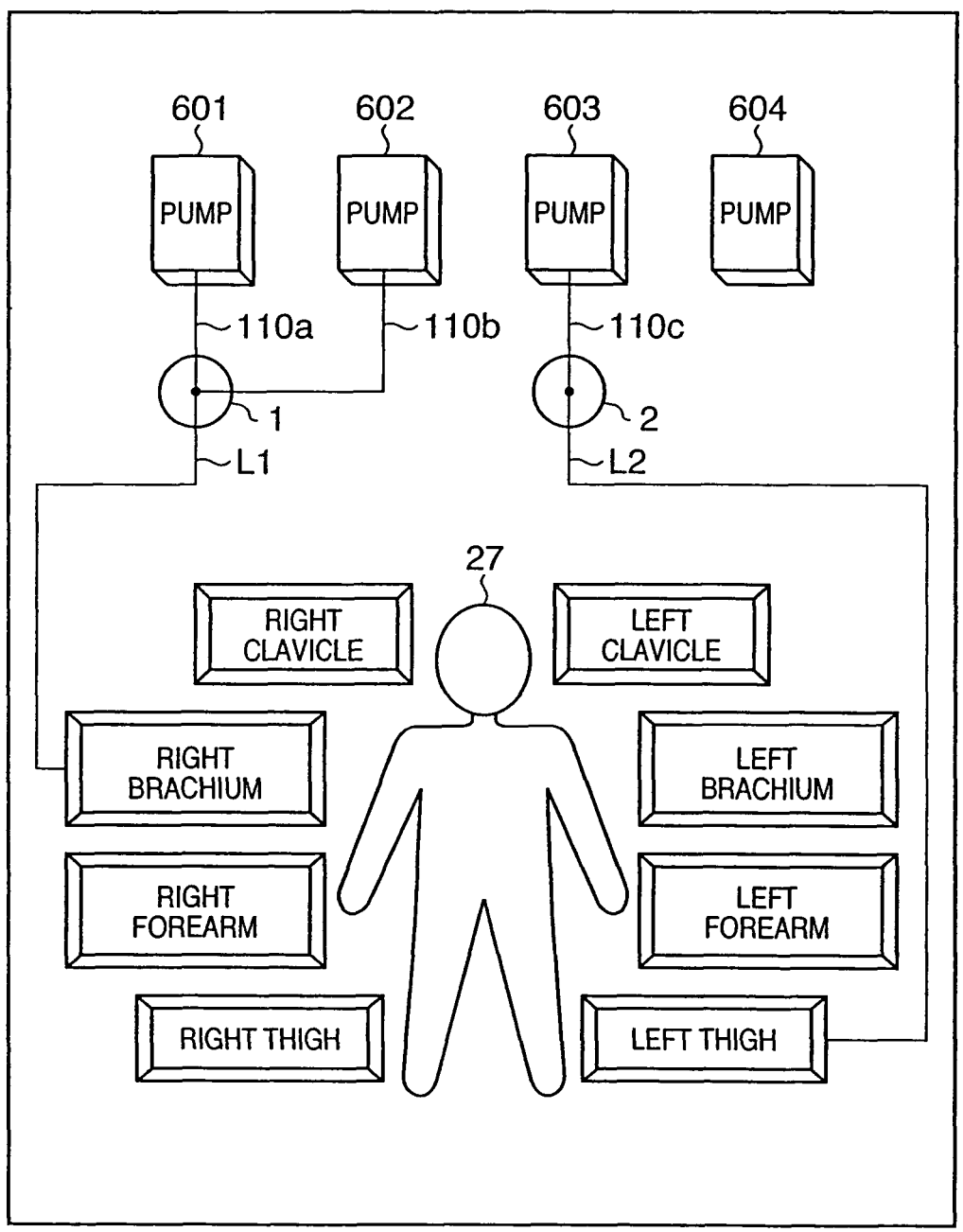
FIG. 7E shows the screen for creating infusion circuitry in the medical pump monitor system in the first embodiment of the present invention.

Subsequently, a line in which the medical pumps 603 and 604 are jointed at some midpoint and a medical fluid is injected into the patient at the left thigh part. The medical pump 603 and the junction production button 614 are clicked one after another, whereby a new junction 2 is displayed below the medical pump 603 with the junction 2 being surrounded by a circle (S1003), and an infusion line 110c is formed in the middle between the medical pump 603 and the junction 2 (FIG. 7D, S1004). Subsequently, this junction 2 and the left thigh part selection button 613 are clicked to form the second infusion line L2 from the junction 2 to the left thigh part of the patient (FIG. 7E, S1018, S1019).

Figure 7F:
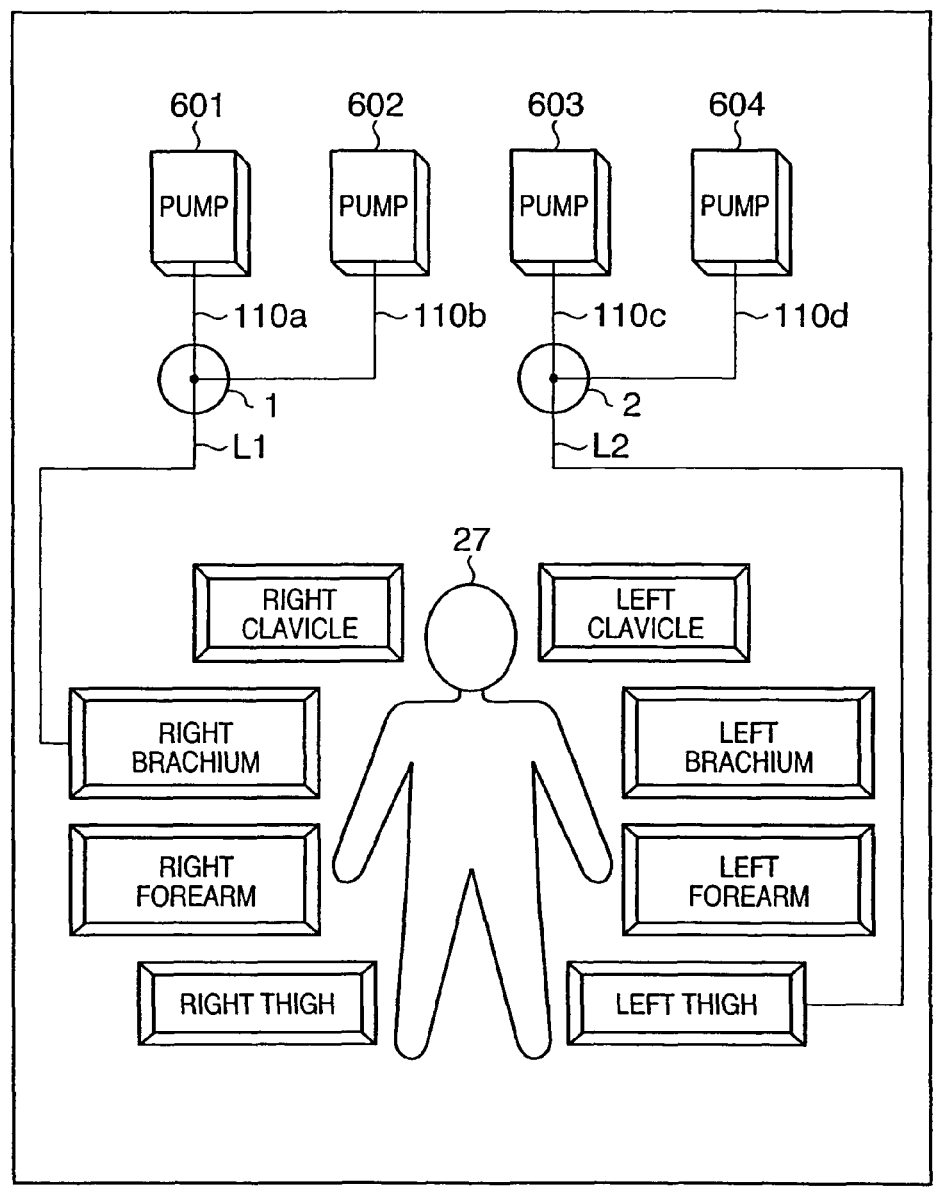
FIG. 7F shows the screen for creating infusion circuitry in the medical pump monitor system in the first embodiment of the present invention.
Figure 7G:
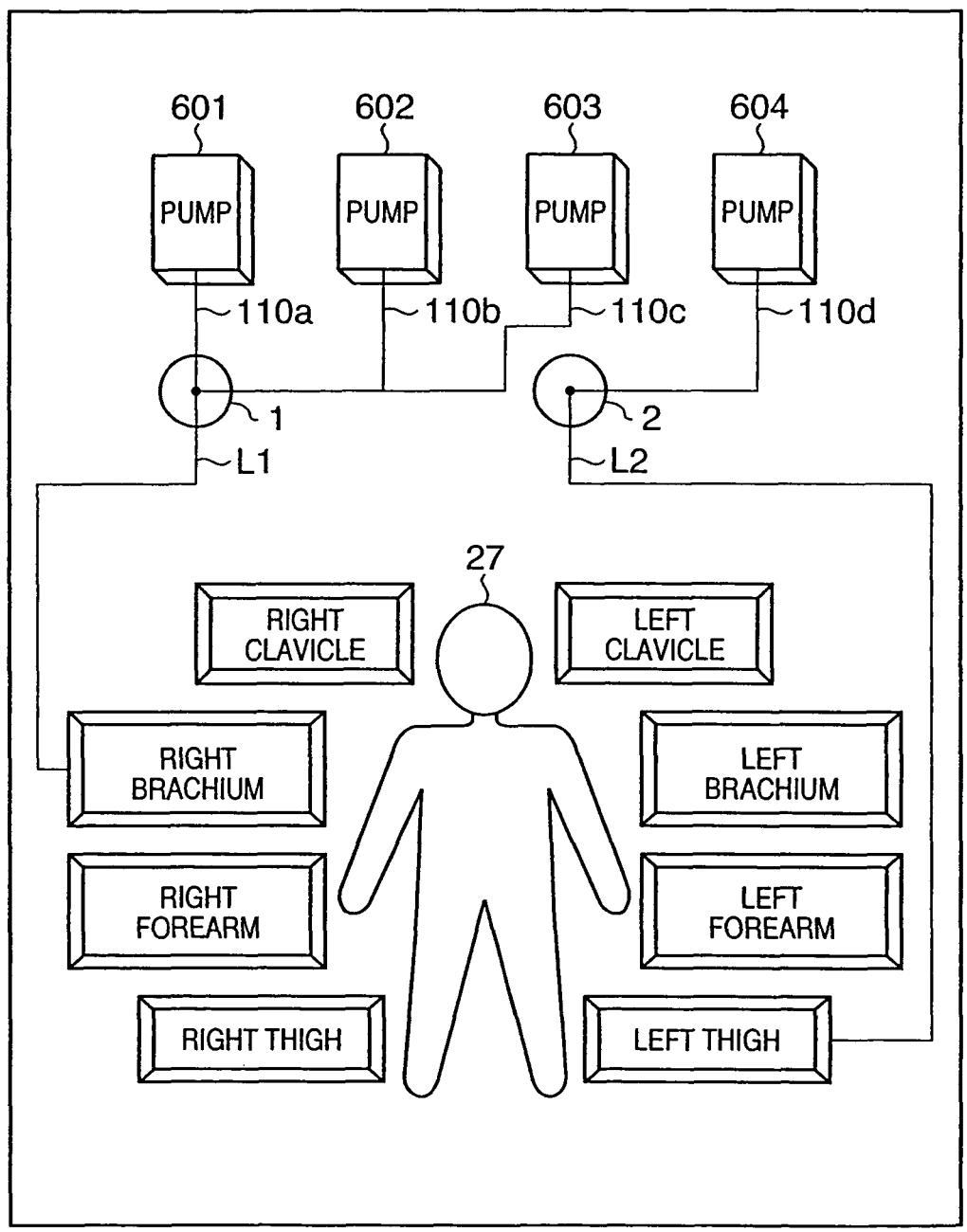
FIG. 7G shows the screen for creating infusion circuitry in the medical pump monitor system in the first embodiment of the present invention.

Finally, the medical pump 604 and the new junction 2 are clicked one after another, thereby completing the infusion line 110c (FIG. 7F, S1018, S1019). At this time, if the operator mistakenly clicks the left thigh part selection button 607 after clicking the medical pump 604, the infusion line L2 from the medical pump 604 will directly run into the left thigh part of the patient without passing through the junction 2. If the operator notices the operational error at this time, he or she may click the return button 615.

The return button is clicked once, whereby finally conducted action (clicking of the left thigh part selection button in this case) is determined as being invalid, and the state in which the medical pump 604 is selected is provided. The operator clicks the right junction at this time, thereby enabling an accurate infusion line to be created. It is also made possible to confirm at a glance the respective medical pumps 601 to 604 and intravenous injection points 606 to 613 of the patient. The operator clicks the end button 616 after confirmation. Through this operation, the created diagram of infusion circuitry is created as a bmp file format, and is stored in the name of "C:¥Yuekic.bmp".

Furthermore, although not described in this embodiment, an interruption button for interrupting processing to end the infusion circuitry creation function may be provided. In this embodiment, the junction is considered as a point, but in the case where transfusion using three-way stop cocks, Yshaped-tubes, Tshaped-tubes and the like is conducted, a three-way stop cock button and a Yshaped-tube button are provided in place of the junction production button, thereby making it possible accommodate the situation.

Also, although only the bit map file is created in this embodiment, the history of operational actions is recorded in other format separately, thereby making it possible to cope flexibly with the situation in which infusion circuitry is slightly changed.

In the aforesaid example, six infusion lines are displayed in FIG. 6. Assuming that display of one infusion line represents one action, six actions of:

(1) drawing a line between the pump 601 and the new junction 1, (2) drawing a line between the junction 1 and the right brachium part of the patient, (3) drawing a line between the junction 1 and the pump 602, (4) drawing a line between the pump 603 and the new junction 2, (5) drawing a line between the junction 2 and the left thigh part of the patient, and (6) drawing a line between the junction 2 and the pump 604 are recorded.

Figure 8:
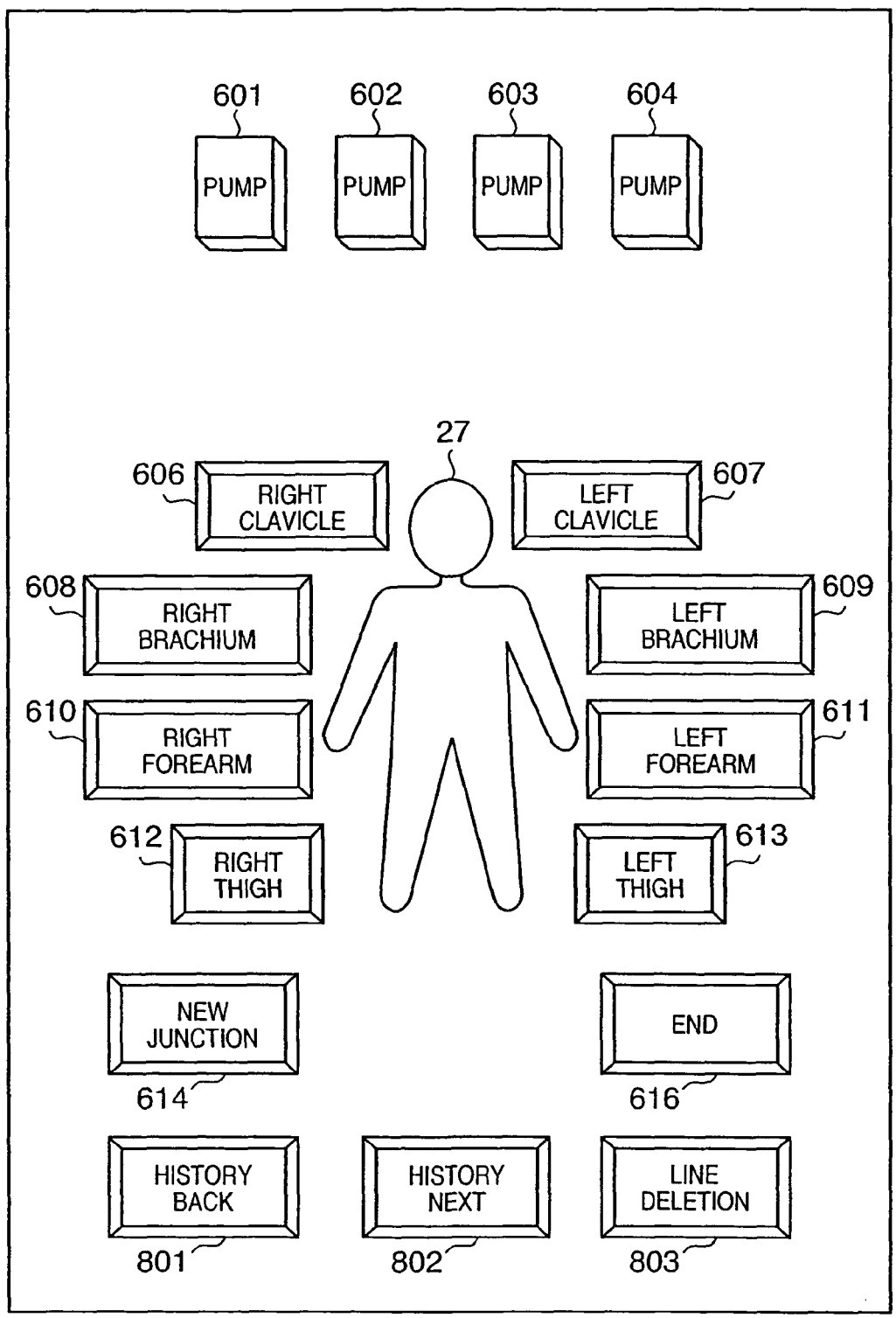
FIG. 8 shows the screen for creating infusion circuitry according to another embodiment in the medical pump monitor system in the first embodiment of the present invention.

The file in which the previous operational action is recorded is read at the time when an infusion circuitry creation window is displayed, the line is drawn in accordance therewith, and selection of each drawing action is enabled, thereby making it possible to cope quickly with the slight modification from the previously created circuitry. Buttons and the like in the window in that case are placed as shown in FIG. 8. In comparison with FIG. 6, the return button is absent, and a history back button 801, a history proceeding button 802 and a line deletion button 803 are newly created.

Each time the history back button is once pushed, the drawn line is selected in reverse chronological order (S1005, S1006). In the case of this embodiment, six lines are displayed at the time when the window appears, and when the history back button is once clicked, the infusion line between the right-hand junction and the pump 604 is selected. When the history back button is selected once again, the state in which the infusion line between the right-hand junction and the pump 604 is selected is released, and the infusion line between the right-hand junction and the left thigh part is selected. At this time, when the history proceeding button 802 is clicked, the state in which the infusion line between the right-hand junction and left thigh part is selected is released, and the infusion line between the right-hand junction and the pump 604 is selected (S1009, S1010). When the line deletion button 803 is clicked with the infusion line selected, the selected infusion line is erased (S1011, S1012).

When a change is to be made from the flood circuitry shown in FIG. 7 so that administration is given by the medical pump 603 to the left-hand junction rather than to the right-hand junction, the history back button is clicked three times after the time when the window appears. Thereby, the line drawn between the medical pump 603 and the right-hand junction is selected. The line deletion button is clicked in this condition, followed by clicking the medical pump 603 and the right-hand junction one after another, whereby the infusion line is drawn between the medical pump 603 and the right-hand junction (FIG. 7G). (In this case, strictly speaking, since the existence of junction between the medical pump 604 and the left thigh part is meaningless, the infusion line between the medical pump 604 and the left-hand junction and the infusion line between the left-hand junction and the left thigh part should be deleted, and then a line between the medical pump 604 and the left thigh part should be drawn as one infusion line, but the junction causes no problems in terms of display.)

At this time, the end button is clicked, whereby a newly modified diagram of infusion circuitry is stored as a bit map file (S1013, S1017). The circle surrounding the junction is displayed in order to allow the operator to select the junction easily, and therefore information of this circle does not need to be stored at the time of storing the diagram as a bit map file.

When the end button pressed, (1) at least two lines should be connected to the junction. (2) The line should not be formed in loop-like shape. (3) Each pump should be necessarily connected to one part of the patient. (4) The number of lines running directly from the pump should be less than two. Determination on these conditions is performed by determining means in the controller (S1014), and processing of displaying an error massage if the condition is satisfied is added (S1015, S1016), thereby making it possible to eliminate operating errors at the time of creating the infusion circuitry diagram and operators' mistakes.

The infusion circuitry creation function is ended after the bit map file is stored (S1017) and normal pump monitor processing is carried out, but at this time, processing of updating the infusion circuitry diagram display region 540 to the new bit map file is carried out.

The administration pass to the patient is selected from a plurality of buttons in this embodiment, but this is for the purpose of easy determination of the position of the line, and if it is desired that more detailed positions are identified, methods in which the number of buttons is further increased, click is made directly on the model picture of the patient, and so on can also be adopted.

In this way, a relatively simple infusion circuitry diagram can be created, but in the case where blood filters and the like are connected in the infusion circuitry, the fluid is passed through an apparatus that is not monitored by the medical pump monitor before being injected, and so on, creation of infusion circuitry diagram by the aforesaid procedure may be complicated. In this case, it can be considered that a handwritten diagram of infusion circuitry is placed near the medical pump to make a check, but there is also a possibility of loss and so on. In this case, it is also possible to read the handwritten diagram of infusion circuitry and display the diagram. The infusion circuitry diagram read function start button 542 is clicked, whereby the scanner 102 is controlled from the controller 100, and the circuitry diagram set in the scanner 102 is read in the system, and is stored in a format as in the case of the creation of infusion circuitry described previously and in the same name of "C:¥Yuekic.bmp". Thereby, the system can create the infusion circuitry diagram using the creation function, and display/manage the diagram without classifying cases either when a registration is made or when the scanner 102 is used to read the diagram for making a registration.

Also, the scanner 102 is used as means for capturing an infusion circuitry diagram such as a handwritten diagram in this embodiment, but it is apparent that similar effects can be obtained by photographing the handwritten infusion circuitry diagram by a digital camera and having the memory medium of the digital camera read by the controller.

It is also possible to use a general graphic drawing application to create an infusion circuitry diagram and store the same as a bit map file, thereby displaying the infusion circuitry created by the graphic drawing application in this system.

According to the medical pump system of the present invention, it is possible to provide a system in which the operation conditions of a plurality of medical pumps are monitored for one patient with a function of creating and editing an infusion line from the pump to the patient on each-by-each basis, and display information created and edited by means of this function displayed on the system, thus making it much easier to confirm (monitor) the current states of infusion lines.

Figure 21A:
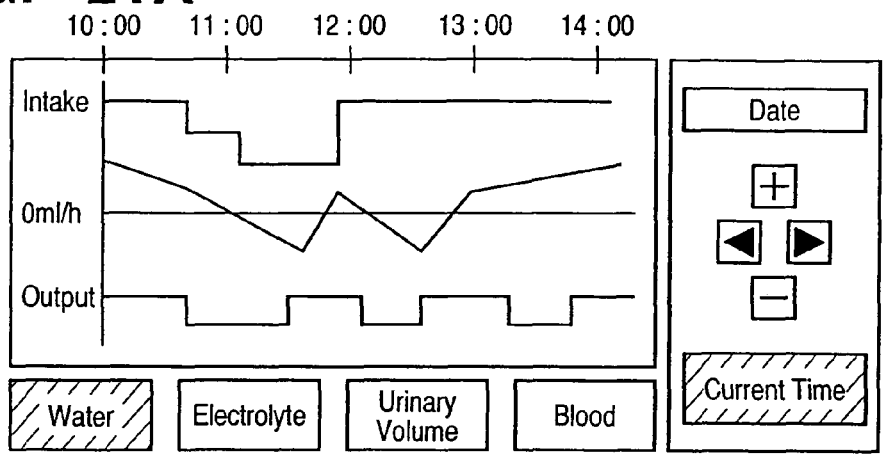
FIGS. 21A to 21C show an example of a monitor screen in the first embodiment of the present invention.
Figure 21B:
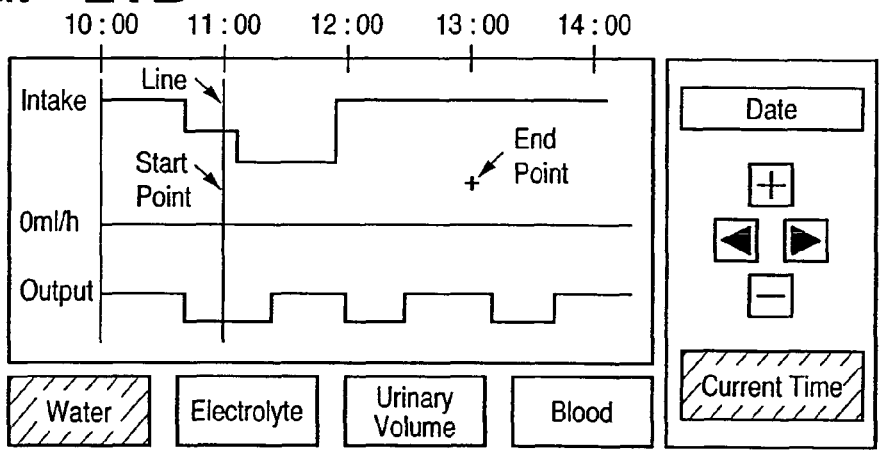
Figure 21C:
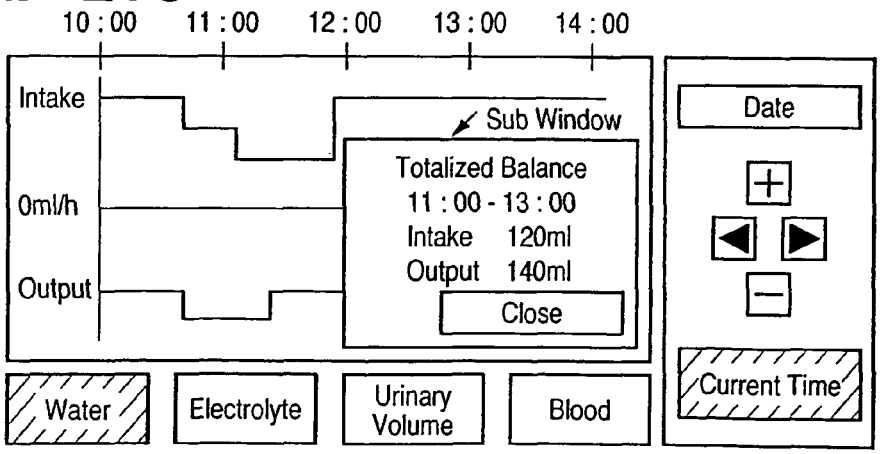

Other functions of the medical pump system of the present invention will be described. FIGS. 21A to 21C show a trend graph of the amount of water displayed after computing the total of the amount of water introduced by all the medical pumps that are used (Intake) and the amount of water discharged as urine (Output) is shown. The range of ml/h can be changed by pressing (clicking) a "+" or "−" key. Also, the amount of water in any time range can be displayed by using "←" or "→". FIG. 21A shows a trend graph of the balance of water (Intake and Output) at the current time. Since it is difficult to understand at a glance the totalized water balance between two arbitrary points (for example, between 11:30 and 13:00) in the graph, two arbitrary points (11:30 and 13:00) are clicked, whereby the balance of the arbitrarily designated segment (between 11:30 and 13:00) can be computed and displayed. The operator first clicks a start point of totalizing computation (11:00 in this case) on the graph. In this figure, when a point near the 11:00 is clicked, a vertical line is displayed in the position of 11:00 (FIG. 21B). Then, when the operator clicks an end point of totalizing computation (13:00 in this case) on the graph (FIG. 21B), a sub-window appears on the graph, and time of totalizing computation and Intake and Output for the arbitrary segment are displayed therein (FIG. 21C). When a "close" button in the sub-window is clicked, the sub-window disappears and the normal state in which the graph is displayed (FIG. 21A) is restored. Also, these totals and trend graphs can be used as diagnostic/therapeutic data at different location by downloading them to the FD 906a or sending them to the host computer or the like through the external port 107a.

Figure 22A:
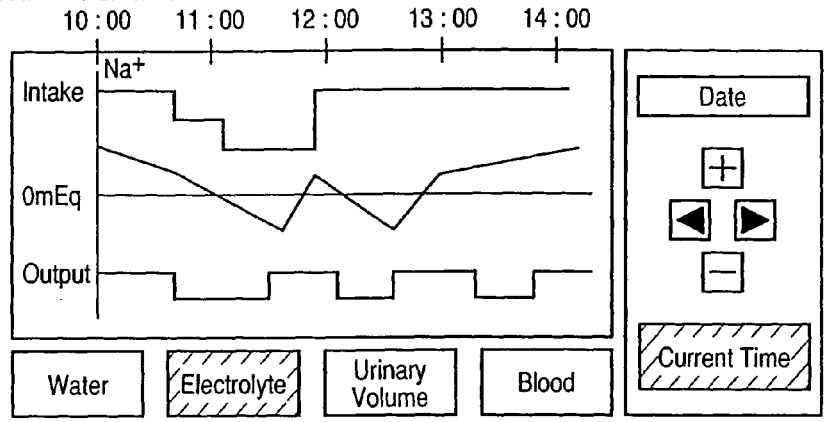
FIGS. 22A to 22C show an example of a monitor screen in the first embodiment of the present invention.
Figure 22B:
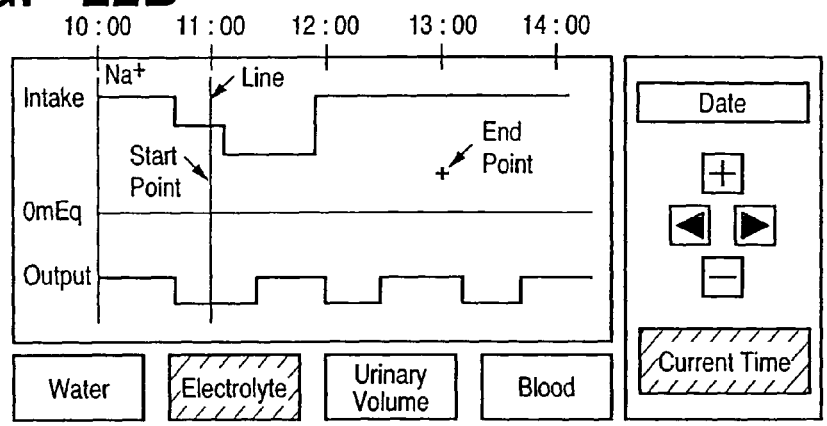
Figure 22C:
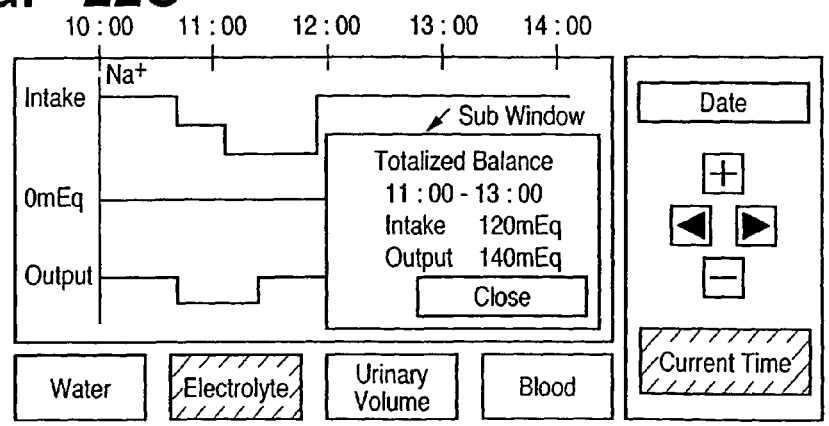

FIG. 22A to 22C show a trend graph of the amount of Na+ as one example of electrolytes displayed after computing the total of the electrolytes (Na$^+$, Ca$^{2+}$, K$^+$, Cl$^-$, etc.) introduced by all the medical pumps that are used or computing the data from the sensor 112. The range of mEg can be changed by pressing a "+" or "−" key. Also, the amount of electrolytes in an arbitrary time range can be displayed by performing operations similar to those in FIGS. 21A to 21C and using "←" and "→". Also, these totals and trend graphs can be used as diagnostic/therapeutic data at different location by downloading them to the FD 906a or sending them to the host computer or the like through the external port 107a. An alarm is given when the amount of the electrolyte exceeds a preset input value (threshold) The screen may be reduced into quarters to display the amounts of four electrolytes of $Na^+$, $Ca^{2+}$, $K^+$, $Cl^-$.

Second Embodiment

The real-time monitoring system of the present invention will be described in detail below, using the drawings. FIG. 11 is a block diagram of the present invention. In FIG. 11, an example of connection of three external apparatuses including medical devises and the like such as infusion pumps, syringe pumps, body pressure monitors, body temperature monitors, urinary volume monitors and electrocardiographs is shown, but this number of apparatuses can be arbitrarily increased or decreased. An external apparatus 1 (1121) is connected through a communication cable to a communication port (external communication unit) 1 (1111) of this system (1105). In a similar way, an external apparatus 2 (1122) and an external apparatus 3 (1123) are connected to a communication port (external communication unit) 2 (1112) and a communication port (external communication unit) 3 (1113), respectively, in a one-to-one correspondence.

Communication ports 1(1111), 2(1112) and 3(1113) are brought together in a communication unit (1104). For the communication unit (1104), a variety of configurations are possible such as a microcomputer control communication board to make connection to a plurality of communication ports and a multiplexer type to switch ports for communication when they are used. Signals obtained from the communication unit (1104) are stored in storing means (1103), and are sent to a comparison unit (1102) simultaneously. The comparison unit compares operation (operating) information of the connected external apparatuses 1(1121), 2(1122) and 3(1123) sent from the communication unit (1104) with operation (operating) information of the previous external apparatuses 1(1121), 2(1122) and 3(1123) stored in the storing unit (1103), and sends a non-change signal to a control unit (1101) if there is no difference, and sends a differential signal to the control unit (1101) if there is a difference. The control unit (1101) changes the contents of the display unit based on the signal from the above described comparison unit. Furthermore, the communication unit (1104) and the communication ports (1111 to 1113) in FIG. 11 correspond to the controller 100 in FIG. 1.

Figure 20:
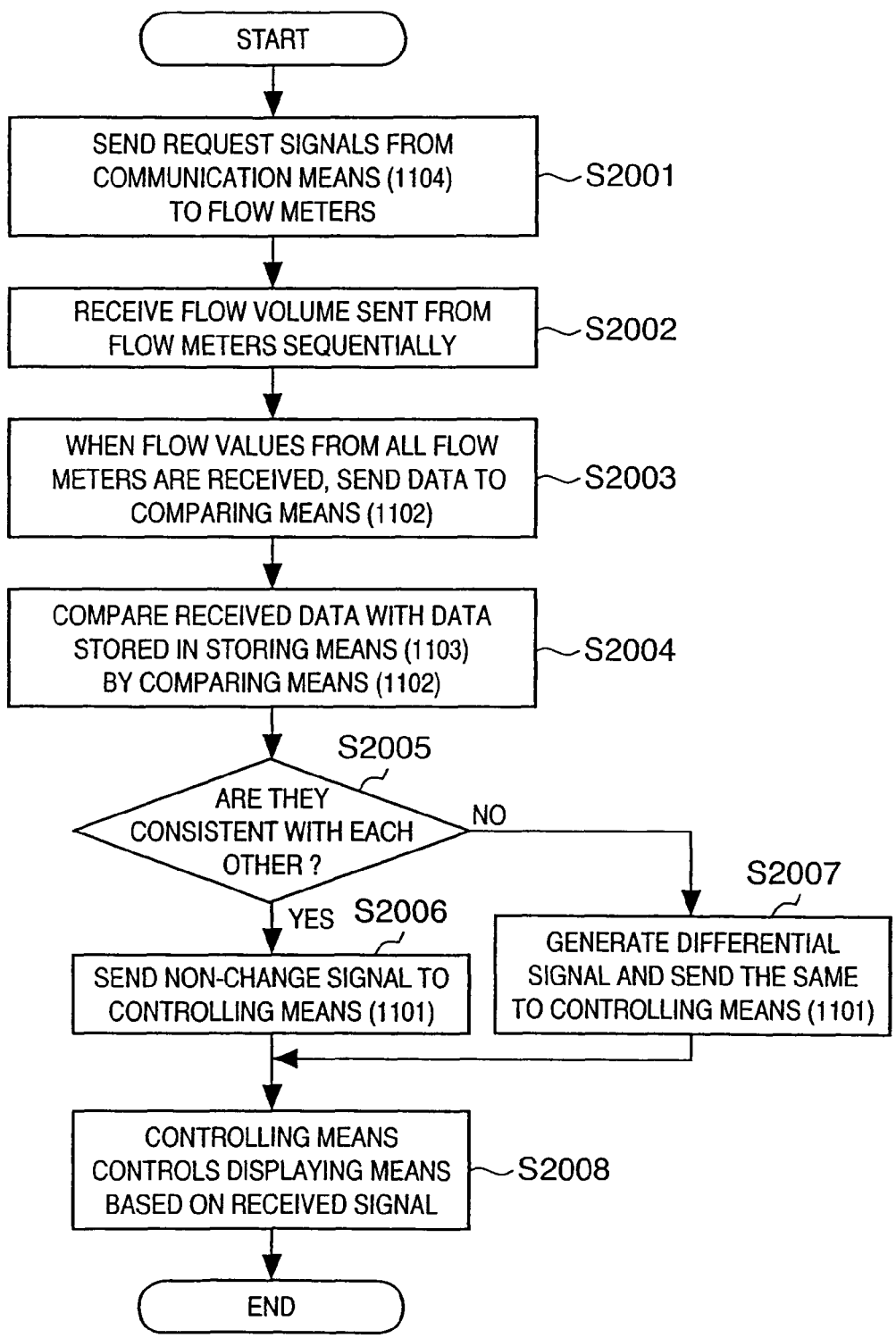
FIG. 20 is a flowchart showing a flow of monitoring processing in the second embodiment of the present invention.

The flow of the present invention will be described further in detail. Presenting as one example a case where three of flow meters for measuring flows of fluids, which represent one type of medical apparatuses, are used as external apparatuses, a system displaying each of the flows and the total flow on the display unit by real time monitoring and a controlling method therefore will be described along with a flowchart shown in FIG. 20. A program corresponding to the flowchart shown in FIG. 20 may be stored in the storing unit (1103) in FIG. 11, or may be provided by a CD-ROM and the like.

Figure 12:
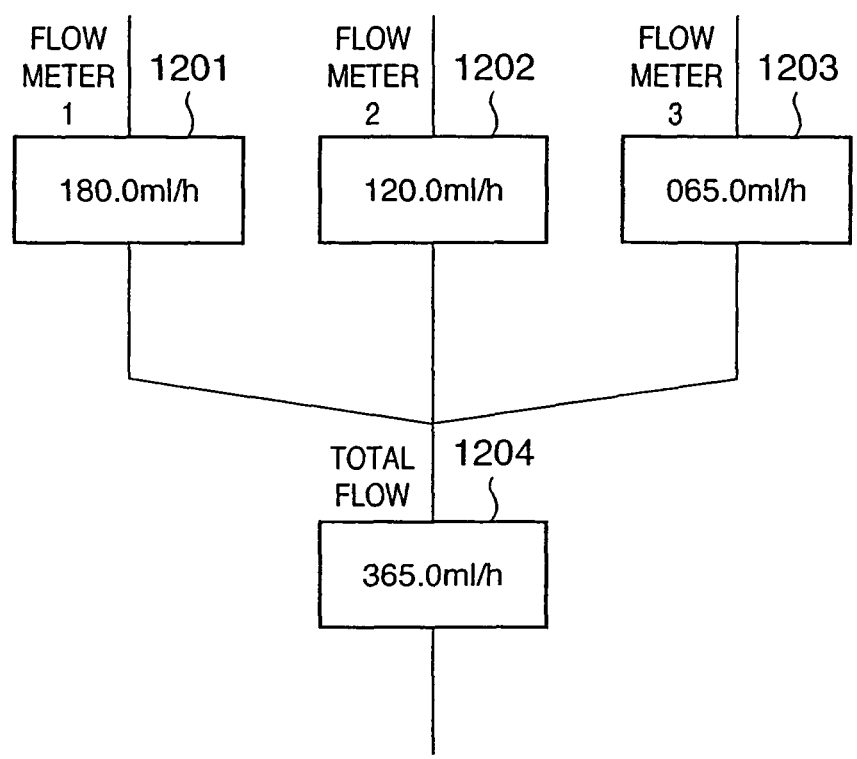
FIG. 12 shows a display screen in the second embodiment of the present invention.

A screen configuration on the display unit 1100 of the system of the present invention is shown in FIG. 12. The flow values of the flow meter 1, of the flow meter 2 and of the flowmeter 3 are displayed in textbox objects 1(1201), 2(1202) and 3(1203), respectively, in such a manner that their actual placement can be visually confirmed. Also, the total flow value obtained by adding up the values of the flow meters 1, 2 and 3 is displayed in a textbox object 4 (1204).

Communication between the system (1105) and the flow meters 1, 2 and 3 will be described as a command respond mode in which the current flow values of the flow meters 1, 2 and 3 are sent back when request signals from the communication unit (1104) are received, but it can also be configured with a mode in which signals from the flow meters 1, 2 and 3 are unilaterally sent to the host system at a fixed time interval in an asynchronous manner, and so on. Furthermore, in actual systems, signals showing the start and end of the signal such as STX and ETX and checksum signals are often added, but these signals are omitted in this embodiment. In this embodiment, flow value signals from the flow meters 1, 2 and 3 show 2-byte numbers of four figures in BCD code with the unit of 0.1 ml/h. For example, the flow value signal shows a flow value of 190.0 ml/h when a 2-byte code of 1900 in hexadecimal digit data is sent.

Figure 13:
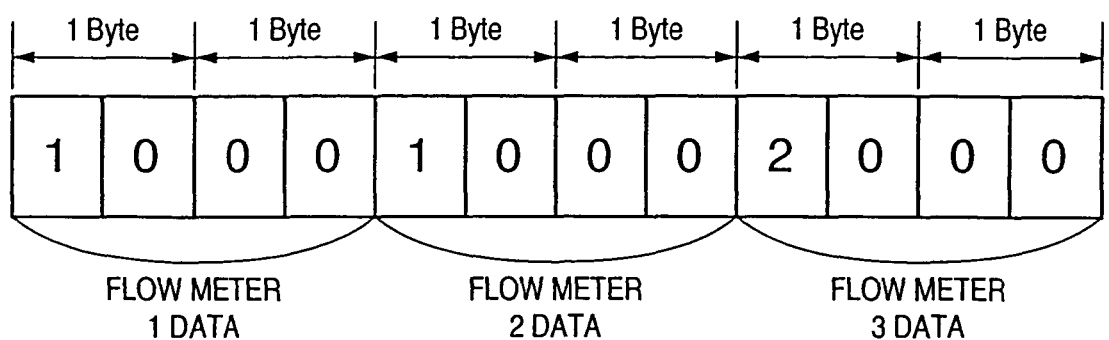
FIG. 13 shows a structure of stored data in a storing unit in the second embodiment of the present invention.

The storing unit (1103) needs an area of six bites in total for storing two bytes of information from three flow meters 1, 2 and 3, respectively. For example, if the flow values of the flow meters 1, 2 and 3 are 100.0 ml/h, 200.0 ml/h and 300.0 ml/h, respectively, information as shown in FIG. 13 is stores in the 6-byte area of the storing unit (1103).

The communication unit (1104) sends request signals to the flow meters 1, 2 and 3 (S2001), performs processing of receiving flow values from the flow meters 1, 2 and 3 for the three flowmeters 1, 2 and 3 one after another (S2002), and sends the data to the comparison unit (1102) at the time of obtaining the flow values from the three flow meters 1, 2 and 3 (S2003).

The comparison unit (1102) compares the signal sent from the communication unit (1104) with the data stored in the storing unit (1103) (S2004), and sends a non-change signal (for example, a hexadecimal digit 1-byte signal of AA in hexadecimal digits) to the control unit (1101) if the data equal each other (S2006). If information of the binary of the flow meters 1, 2 and 3 stored in the storing unit (1103) is of 1000 in hexadecimal digits, the signal sent from the communication unit (1104) is of 1200 in hexadecimal digits, a 3 byte-signal of 021200 in hexadecimal digits is sent to the control unit (1101). The "02" equivalent to the first byte number in this case is a number corresponding to the connected flow meters 1, 2 and 3, and if the flow meter of which flow value is changed is the flow meter denoted by 3, this value will be "03". As described above, the differential signal is represented by "external apparatus number"+"flow value" in the embodiment.

Figure 14:
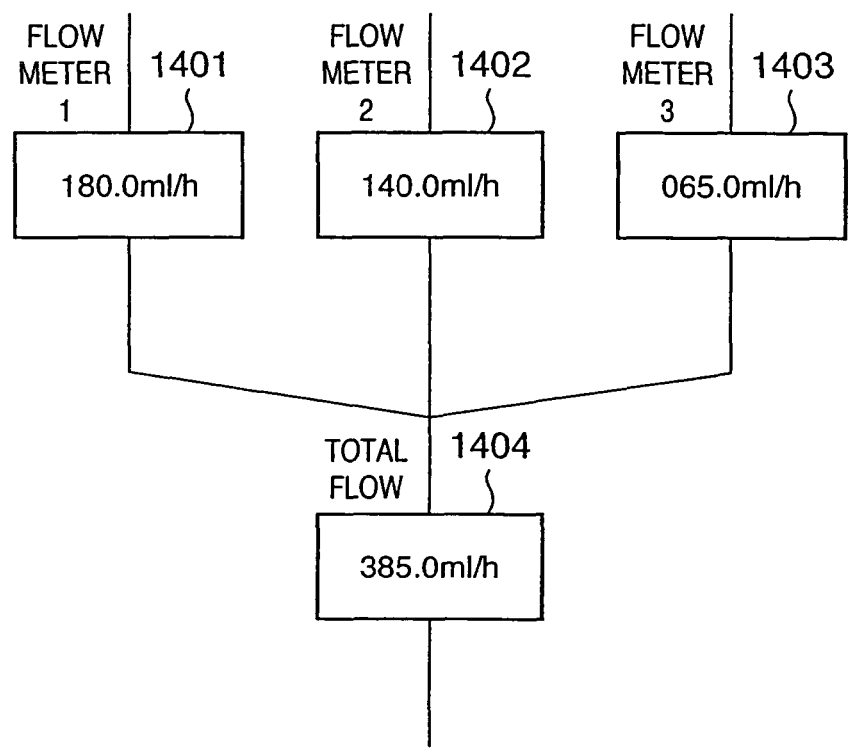
FIG. 14 shows a display screen of real time monitoring in the second embodiment of the present invention.

The control unit (1101) does not perform change/control of the display unit (1100) if the signal from the comparison unit (1103) is a non-change signal, and if a signal with the flow changed is sent, the control unit (1101) sends to the display unit (1100) processing instructions to change the displayed contents of the display unit (1100) based on the signal with the flow changed. If a signal of 021400 in hexadecimal digits is sent from the comparison unit (1102) when the contents shown in FIG. 12 are displayed on the display unit (1100), the contents of the display unit (1100) are rewritten to those as shown in FIG. 14. Specifically, the contents of the textbox 2 (1402) are rewritten from 120.0 ml/h to 140.0 ml/h, and following this change, the total flow value in the textbox object 4 (1404) is rewritten 365.0 ml/h to 385.0 ml/h.

The signal with the flow changed is represented by "the number of the flow meter with the flow changed"+"the flow value after changing" in the embodiment, but in the case where values of two or more flow meters are changed, two signals put together may be sent. For example, if the flow value of the flow meter 1 is changed from 90.0 ml/h to 100.0 ml/h, and the flow value of the flow meter 3 is changed from 120.0 ml/h to 80 ml/h, a 6-byte signal of 011000030800 in hexadecimal digits may be sent as for a signal that is sent from the comparison unit to sending means.

Also, in the above described case, since the byte number of the differential signal varies depending on the number of external apparatuses with the flow value changed in such a manner that when the numbers of external apparatuses with the flow value changed are one, two and three, the byte numbers of the differential signal are 3 bytes, 6 bytes and 9 bytes, respectively, the control unit (101) of a master needs processing consistent with the byte number of the differential signal, thus putting a burden on information processing (signal processing). Then, in stead of sending selectively the flow value of the external apparatus with the flow value changed, all the flow values among the external apparatuses 1(1121), 2(1122) and 3(1123) may be sent if at least one of all the flow values of the external apparatuses 1(1121), 2(1122) and 3(1123) is changed. In this case, since the byte number of the differential signal is constant 9 bytes, a burden on information processing (signal processing) can be reduced. Furthermore, for whether all the flow values are sent or the flow value subjected to change is selectively sent, changes can be made as appropriate depending on the number of external apparatuses connected to the system (1105), the frequency of changing external apparatuses and the importance of patient monitor information.

As described above, in this system (1105), operation information (operation signals) among the external apparatuses 1(1121), 2(1122) and 3(1123) are received in succession, and past operation information stored in the storing unit (1103) and operation information currently received from the external apparatuses 1(1121), 2(1122) and 3(1123) are outputted. The comparison unit (1102) compares the past operation information with the current operation information, generates information (differential information) showing a difference between the past operation information and the current operation information and sends the information to the control unit (1101). Thereby, the control unit may avoid performing change/control of the display unit unless there is no substantial difference, thus making it possible to reduce a burden on information processing even if a large number of external apparatuses such as medical pumps are used. Furthermore, the information showing a difference (differential information) is constituted at least by the aforesaid external apparatus number (information indicating an external apparatus sending current information different from the past information it sent), whereby the amount of information to be sent to the control unit can be reduced as compared with operation information from the external apparatus, and this reduction of the amount of information also makes it possible to reduce a burden on information processing (signal processing) in the control unit. If the communication unit sends repeatedly request signals for requesting information from the external apparatuses 1(1121), 2(1122) and 3(1123) in predetermined timing, the control unit does not need to dispatch the request signal, thereby making it possible to reduce a burden on information processing (signal processing) in the control unit. Consequently, a monitoring system can be built, which causes no drop in response when the control unit concurrently performs processings of the keyboard and various kinds of switches (not shown) as HMI (Human Machine Interface).

Furthermore, the contents in the storing unit (1103) is set 0 (or data outside the normal range) at the time of starting the system, whereby the data of all the flow meters are sent to the control unit (1101) because the data of the flow meters 1, 2 and 3 obtained from the communication unit (1104) are different from the information stored in the storing unit (1103), and the latest flow values of the flow meters are automatically displayed on the display unit (1100) when the system starts.

There are cases where information from the flow meters 1, 2 and 3 is not constituted by just flow values, but alarm information of the flow meters 1, 2 and 3 and the like are added thereto to increase the amount of information. In that case, comparison time and the amount of information to be stored are reduced in the control unit (1101) and in the storing unit (1103), respectively, thereby making it possible to achieve speed enhancement of processing associated with reduction in volume of comparison and a drop in price associated with reduction in storage memory areas. Specific methods thereof will be described using FIGS. 15, 16 and 17.

Figure 15:
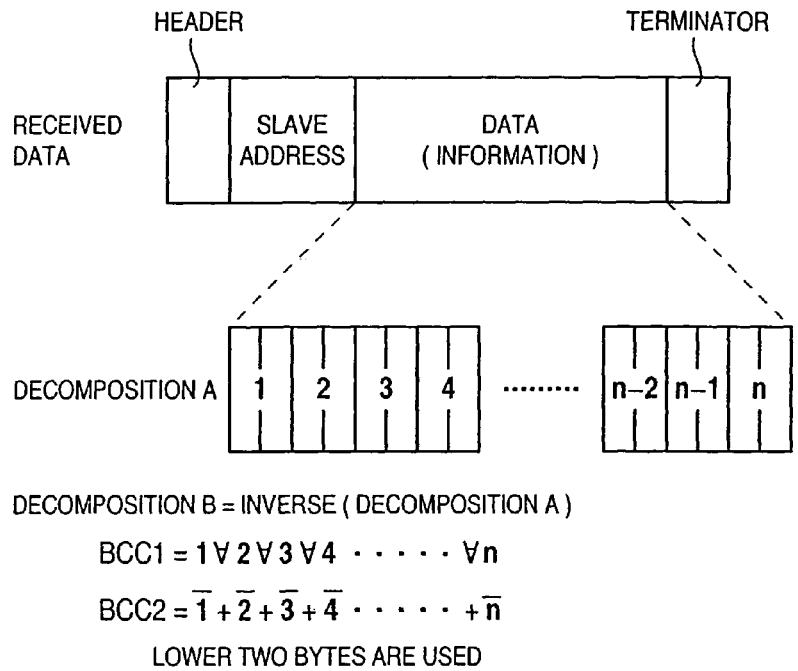
FIG. 15 shows an inverse data check system in the second embodiment of the present invention.
Figure 16:
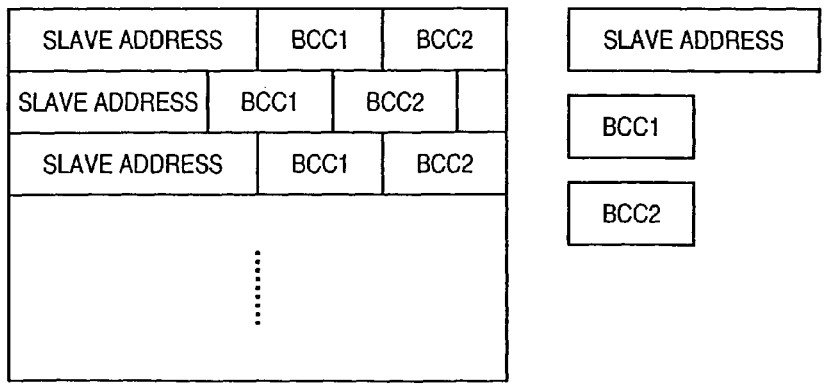
FIG. 16 shows an inverse data check system in the second embodiment of the present invention.

In FIG. 15, communication data obtained by the communication unit in the case of large amount of information is shown. In communication data, a slave address showing a number of a slave (external apparatus) and data comprised of operation conditions of slaves are exist between a header such as STX and a terminator such as ETX. First, data such as operation conditions are decomposed out of received data (decomposition A). Coding by exclusive OR (XOR) (BCC: Block Check Character) is performed for data of this decomposition A by each word from the heading, what is finally produced is considered as BCC 1 (Type I transformation). Furthermore, with an inverse (NOT) of the decomposition A is being decomposition B, and coding by summation by each word (ADD) is performed for data of this decomposition B, and what is finally produced is considered as BCC 2 (Type II transformation). These adopt lower 16 bits. Data change is considered to have occurred, from changes in BCC1 and BCC2. BCC coding is generally used and its reliability is acknowledged, but further coding processing is performed using reversed data in calculation, and two BCCs having no causal relation are compared with each other, thereby improving safety. Due to this safety, the amount of data can be reduced as shown in FIG. 16 without storing all received data to shorten memory access time. Also, if the received signal includes BCC in advance, the BCC data is directly used, whereby the above described decomposition work and calculation processing can be reduced and further enhancement of the speed can be expected.

Figure 17:
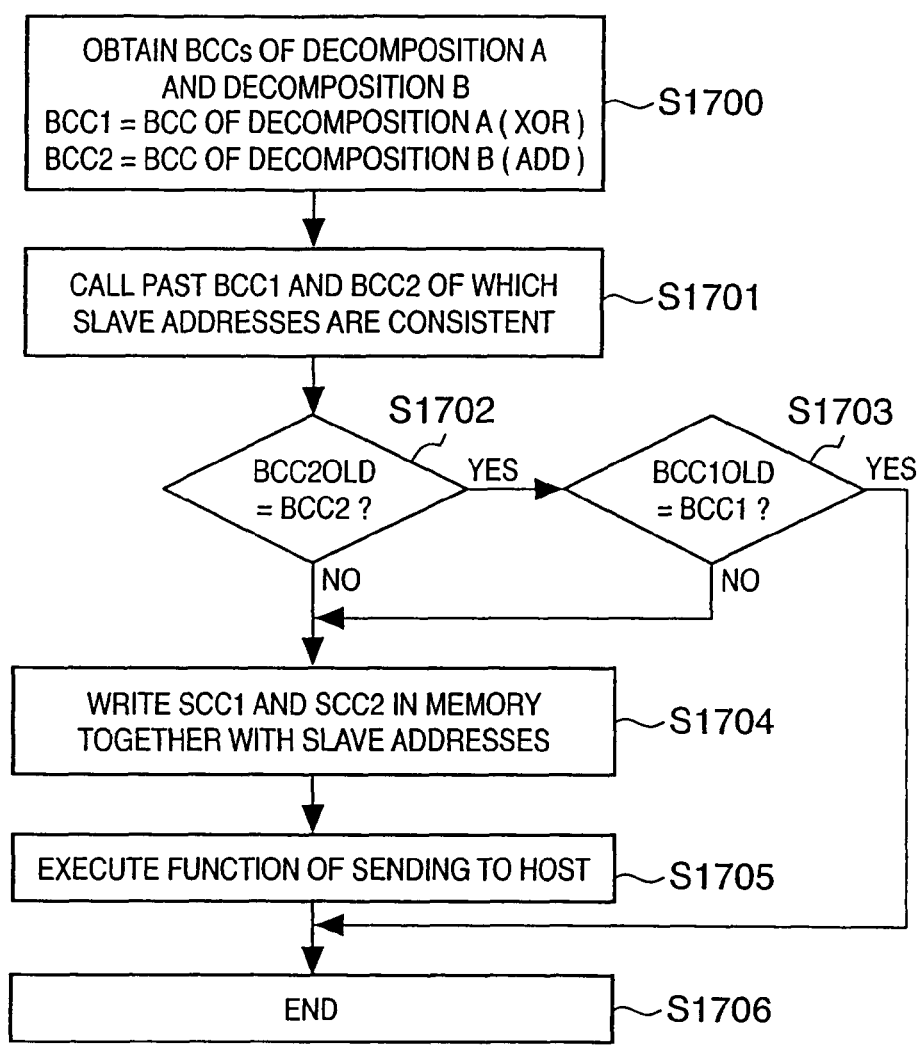
FIG. 17 shows an inverse data check system in the second embodiment of the present invention.

A series of the flow thereof will be described using FIG. 17. A portion of data in which the operation conditions of slaves and the like (decomposition A) is fetched out of the communication data, and XOR computation of 16 bits thereof is performed to provide BCC1. Also, with an inverse of decomposition A being decomposition B, lower 16 bits resulting from ADD computation of decomposition B are considered as BCC2 (Step S1700). A slave address is read from the communication data, and the past BCC1 and BCC2 corresponding to this address are read from the storing unit (1103) (Step S1701). The current BCC2 is compared with the past BCC2 read from the storing unit, and advancement to Step S1704 is made if their contents are different from each other, and advancement to Step S1703 is made if their contents are identical to each other (Step S1702). If their contents are identical to each other in Step S1702, the current BCC1 is compared with the past BCC1 read from the storing unit (1103), and advancement to Step S1704 is made if their contents are different from each other, and processing is ended without communicating with the host based on the assumption that the communication condition for the slave address remains unchanged if their contents are identical to each other (Step S1706). If the current data and the past data are different from each other in Step S1702 and Step S1703, BCC1 and BCC2 are written along with the corresponding slave address (Step S1704). Information of change of operation conditions and the like is sent to the external apparatus corresponding to the slave address (Step S1705) and processing is ended (Step S1706). By performing such processing, the number of bytes to be subjected to comparison can be reduced to shorten processing time, data to be stored can be reduced to the minimum to speed up time of read/write in the storing unit (1103), and communication time can also be reduced because only data associated with change in slaves is sent to the host. Furthermore, a protocol such that no signals are sent to the host in the case of no changes is presented in FIG. 17, but it is easy to make a modification thereto so that a short non-signal change is sent.

Figure 18:
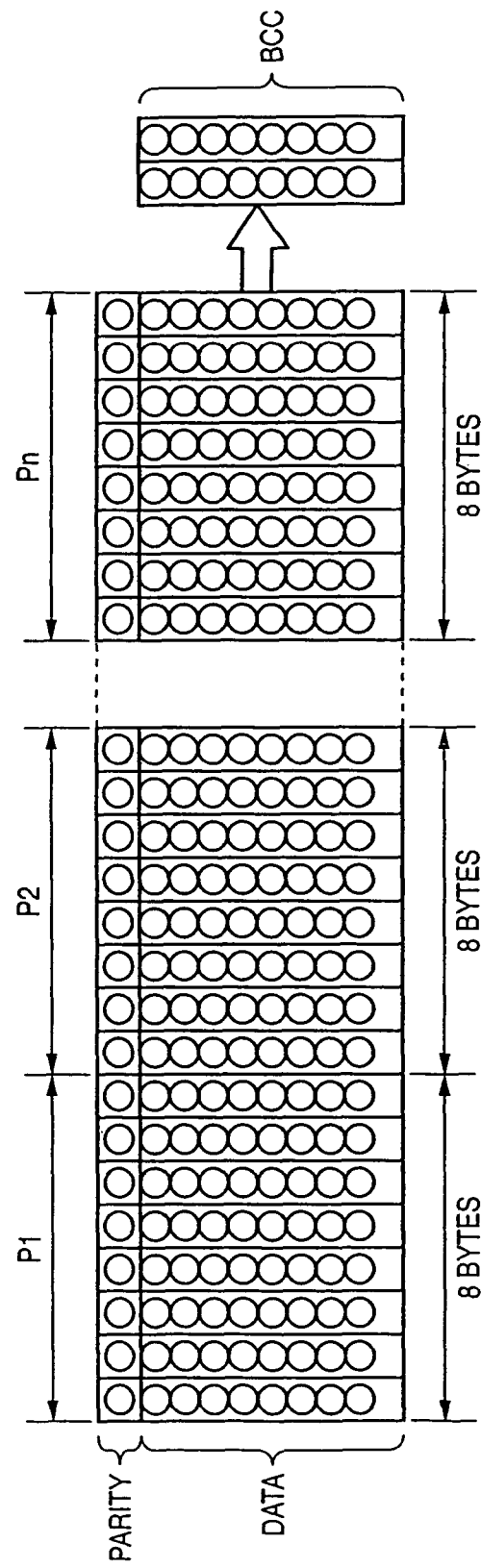
FIG. 18 shows a method of detecting a position in which data is changed in the second embodiment of the present invention.
Figure 19:
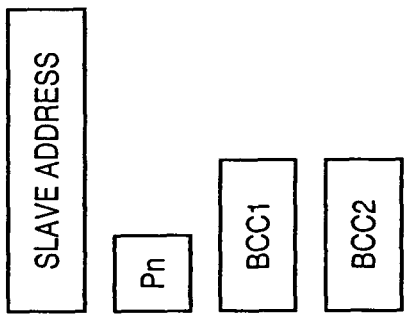
FIG. 19 shows a method of detecting a position in which data is changed in the second embodiment of the present invention.

If information further increases, in addition to comparison BCC1 and BCC2 in the previous example, parity data (equivalent data) of each data is stored, and its change is detected, thereby making it possible to make a quick check on which portion of communication data has data subjected to change. FIGS. 18 and 19 show a method of detecting the position of changed data. Structures of BCC data and parity data for data such as the operation condition of the slave are shown in FIG. 18. Processing is performed as in the case of FIG. 15 in the previous example with respect to BCC, and for this data, parity data having parity codes corresponding to the bit of each 1-byte data put together on an eight-by-eight basis is also to be checked as data of the vertical component, in addition to the lateral check system. Stored contents in the storing unit (1103) when such a method of detecting the position of changed data are shown in FIG. 19. Parity data are aligned in succession after each slave address, and after that, BCC1 and BCC2 similar to those shown in FIG. 16 are stored. In this example, parity data are data of P1, P2, P3 and Pn. Pn increases/decreases with the increase/decrease of communication data 8 bytes. The processing flow thereof is similar to that shown in FIG. 17, if it is determined in Step S1702 and Step S1703 that the past BCC data and the current BCC data are different from each other, past parity data is compared with current parity data for each parity data before the BCC data is written in the memory, parity data with difference found and the BCC data are written in a corresponding memory area, and the data and the slave address corresponding to the parity subjected to change are selectively sent to the host. Specifically, the flow value of the slave for initial 8 bytes of the data, information associated with supplied voltage of the flow meter for next 8 bytes of the data, alarm information associated with the number of rotations of the apparatus for subsequent 8 bytes of the data, and continuous operation time for final 8 bytes of the data are sent. If difference is found for the parity of the third byte in a slave, only alarm information associated with the number of rotations for a corresponding slave address may selectively be sent, and thus host sending time can be reduced significantly, leading to reduction in total time.

In this way, according to the real-time monitoring system and the controlling method therefore and the program storage medium of the present invention, operation states, alarm information, etc. of external apparatuses including a plurality of medical apparatuses such as infusion pumps, syringe pumps and blood pressure monitors having a large amount of send data can be monitored in real time.

The present invention is not limited to the above embodiments and various changes and modifications can be made within the spirit and scope of the present invention. Therefore, to apprise the public of the scope of the present invention, the following claims are made.

What is claimed is:

1. A medical pump monitoring system which administers medical fluids and the like for a patient using a plurality of medical pumps, and monitors flows of delivered fluids and alarm information of the medical pumps by wired communication and/or wireless communication, the medical pump monitoring system comprising:
   a control unit;
   a display unit;
   an infusion circuitry creating unit for creating infusion circuitry data defining connection conditions of infusion lines from the plurality of medical pumps, and administration passes and/or administration positions for the patient;
   said control unit controlling said display unit to display the created infusion circuitry data with information from the plurality of medical pumps connected according to the created infusion circuitry data, in a pump information display area on a monitor screen of said display unit according to operations from an operator of the medical pump monitoring system; and
   the pump information display area including,
      an area for displaying respective operation conditions of different ones of the medical pumps in a visually distinguishing manner, wherein at least a normal operation condition is visually indicated in a first manner by a first color, an alarm condition is indicated by a second color which is visually distinguishable from the first color, an interruption of the administration operation is indicated by a third color which is visually distinguishable from the first color and the second color, and a condition where the medical pump is not connected is indicated by a fourth color which is visually distinguishable from the first color, the second color and the third color,
      areas for displaying respective flow amounts of the medical pumps,
      areas for displaying respective alarm information for medical pumps,
      areas for displaying respective administered drug information for medical pumps,
      an area for displaying the infusion circuitry for delivery medical fluids to the patient according to the created infusion circuitry data, and
   wherein said infusion circuitry creating unit displays a diagram of the patient to receive the administration position for the patient from the operator.

2. The medical pump monitoring system according to claim 1, wherein said infusion circuitry creating unit further comprises a determination unit for determining whether or not the infusion line is suited to a practical method for transfusion.

3. The medical pump monitoring system according to claim 2, wherein said determination unit determines whether or not a loop-shaped line in the infusion line exists, and if so, gives an alarm to the operator.

4. The medical pump monitoring system according to claim 2, wherein said determination unit determines whether or not two or more of the infusion lines are directly connected to a single medical pump, and if so, gives an alarm to the operator.

5. The medical pump monitoring system according to claim 2, wherein said determination unit determines whether or not the infusion line is ended at some midpoint without reaching the patient, and if so, gives an alarm to the operator.

6. The medical pump monitoring system according to claim 2, wherein said determination unit determines whether or not the infusion line is formed towards at least one position of the patient from the medical pump, and if so, gives an alarm to the operator.

7. The medical pump monitoring system according to claim 2, wherein said determination unit determines whether or not the infusion line inserted into a specified portion of the patient is inserted into the patient again, and if so, gives an alarm to the operator.

8. The medical pump monitoring system according to claim 2, wherein said determination unit determines whether or not the infusion line from the operating medical pump is not connected to the patient, and if so, gives an alarm to the operator.

9. The pump monitoring system according to claim 1, further comprising,
- a reading unit for reading an infusion circuitry diagram, including a handwritten diagram, in the medical pump monitoring system,
- wherein, the infusion circuitry data to be displayed on the monitor screen during operation of the medical pump monitoring system is selected from the data created by the infusion circuitry creating unit and the data read by reading unit, according to the operation from the operator.

10. The medical pump monitoring system according to claim 1, wherein said infusion circuitry creating unit selects an optimal pump arrangement pattern from a plurality of pump arrangement patterns registered in advance.

11. The medical pump monitoring system according to claim 1, wherein the monitor screen displays thereon real-time states or trends in arbitrary time ranges for at least any one of the amount of water, the urinary volume and the amount of electrolytes.

* * * * *